(12) United States Patent
Lukyanenko et al.

(10) Patent No.: US 11,596,339 B2
(45) Date of Patent: Mar. 7, 2023

(54) DETERMINING INTENDED USER MOVEMENT TO CONTROL AN EXTERNAL DEVICE

(71) Applicant: Case Western Reserve University, Cleveland, OH (US)

(72) Inventors: Platon Lukyanenko, Shaker Heights, OH (US); Matthew R. Williams, Cleveland, OH (US); Dustin J. Tyler, Highland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 379 days.

(21) Appl. No.: 16/818,185

(22) Filed: Mar. 13, 2020

(65) Prior Publication Data

US 2020/0289016 A1 Sep. 17, 2020

Related U.S. Application Data

(60) Provisional application No. 62/817,785, filed on Mar. 13, 2019.

(51) Int. Cl.
*A61B 5/296* (2021.01)
*G06F 3/01* (2006.01)
*A61F 2/72* (2006.01)
*A61B 5/00* (2006.01)

(52) U.S. Cl.
CPC ............ *A61B 5/296* (2021.01); *A61B 5/4851* (2013.01); *A61F 2/72* (2013.01); *G06F 3/015* (2013.01)

(58) Field of Classification Search
CPC ......... A61B 5/296; A61B 5/4851; A61F 2/72; G06F 3/015; G06F 3/017
See application file for complete search history.

(56) References Cited

U.S. PATENT DOCUMENTS

| | | | | |
|---|---|---|---|---|
| 2008/0009771 | A1* | 1/2008 | Perry | A61H 1/0281 600/587 |
| 2018/0020951 | A1* | 1/2018 | Kaifosh | A61B 5/378 607/48 |
| 2018/0311054 | A1* | 11/2018 | Schroeder | A61F 2/50 |

OTHER PUBLICATIONS

Roche, Aidan D., et al. "Prosthetic myoelectric control strategies: a clinical perspective." Current Surgery Reports 2.3 (2014): 44.
(Continued)

*Primary Examiner* — Alexander Eisen
*Assistant Examiner* — Kebede T Teshome
(74) *Attorney, Agent, or Firm* — Tarolli, Sundheim, Covell & Tummino LLP

(57) ABSTRACT

A user-specific model of muscular activity can be used to control an external device based on muscular activity within a limb of a user. The user-specific model of muscular activity can include single movements and corresponding one or more primary muscle patterns. New single movements can be added to the user-specific model of muscular activity can be by a system that includes a processor by receiving user-specific EMG signals (including one or more EMG patterns that indicate a single movement); decomposing the user-specific EMG signals into the one or more EMG patterns in EMG feature space that indicate the single movement; and updating the user-specific model of muscular activity to include the single movement and corresponding one or more primary muscle patterns based on the one or more EMG patterns in EMG feature space.

21 Claims, 17 Drawing Sheets

(56) References Cited

OTHER PUBLICATIONS

Atkins, Diane J., Denise CY Heard, and William H. Donovan. "Epidemiologic overview of individuals with upper-limb loss and their reported research priorities." Jpo: Journal of prosthetics and orthotics 8.1 (1996): 2-11.

Page, David Michael. Restored hand sensation in human amputees via Utah slanted electrode array stimulation enables performance of functional tasks and meaningful prosthesis embodiment. Diss. The University of Utah, 2016.

Marasco, Paul D., et al. "Illusory movement perception improves motor control for prosthetic hands." Science translational medicine 10.432 (2018).

Ortiz-Catalan, Max, Bo Håkansson, and Rickard Brånemark. "An osseointegrated human-machine gateway for long-term sensory feedback and motor control of artificial limbs." Science translational medicine 6.257 (2014): 257re6-257re6.

Hudgins, Bernard, Philip Parker, and Robert N. Scott. "A new strategy for multifunction myoelectric control." IEEE transactions on biomedical engineering 40.1 (1993): 82-94.

Hahne, Janne M., et al. "Linear and nonlinear regression techniques for simultaneous and proportional myoelectric control." IEEE Transactions on Neural Systems and Rehabilitation Engineering 22.2 (2014): 269-279.

Cipriani, Christian, et al. "Online myoelectric control of a dexterous hand prosthesis by transradial amputees." IEEE Transactions on Neural Systems and Rehabilitation Engineering 19.3 (2011): 260-270.

Hahne, J. M., et al. "Simultaneous and proportional control of 2D wrist movements with myoelectric signals." 2012 IEEE international workshop on machine learning for signal processing. IEEE, 2012.

Ishii, Chiharu, et al. "Control of myoelectric prosthetic hand based on surface emg." 2011 IEEE International Conference on Mechatronics and Automation. IEEE, 2011.

Jiang, Ning, et al. "Intuitive, online, simultaneous, and proportional myoelectric control over two degrees-of-freedom in upper limb amputees." IEEE transactions on neural systems and rehabilitation engineering 22.3 (2013): 501-510.

Nielsen, Johnny LG, et al. "Enhanced EMG signal processing for simultaneous and proportional myoelectric control." 2009 Annual International Conference of the IEEE Engineering in Medicine and Biology Society. IEEE, 2009.

Simon, Ann M., et al. "A decision-based velocity ramp for minimizing the effect of misclassifications during real-time pattern recognition control" IEEE Transactions on Biomedical Engineering 58.8 (2011): 2360-2368.

Jiang, Ning, et al. "EMG-based simultaneous and proportional estimation of wrist/hand kinematics in uni-lateral trans-radial amputees" Journal of neuroengineering and rehabilitation 9.1 (2012): 42.

Jiang, Ning, Kevin B. Englehart, and Philip A. Parker. "Extracting simultaneous and proportional neural control information for multiple-DOF prostheses from the surface electromyographic signal." IEEE transactions on Biomedical Engineering 56.4 (2008): 1070-1080.

Kapelner, Tamás, et al. "Classification of motor unit activity following targeted muscle reinnervation." 2015 7th International IEEE/EMBS Conference on Neural Engineering (NER). IEEE, 2015.

Cavanagh, Peter R., and Paavo V. Komi. "Electromechanical delay in human skeletal muscle under concentric and eccentric contractions" European journal of applied physiology and occupational physiology 42.3 (1979): 159-163.

Englehart, Kevin, and Bernard Hudgins. "A robust, real-time control scheme for multifunction myoelectric control." IEEE transactions on biomedical engineering 50.7 (2003): 848-854.

Artemiadis, Panagiotis K., and Kostas J. Kyriakopoulos. "EMG-based control of a robot arm using low-dimensional embeddings " IEEE Transactions on Robotics 26.2 (2010): 393-398.

Matrone, Giulia C., et al. "Real-time myoelectric control of a multi-fingered hand prosthesis using principal components analysis." Journal of neuroengineering and rehabilitation 9.1 (2012): 40.

Lock B. A., K. Englehart, and B. Hudgins. "Real-time myoelectric control in a virtual environment to relate usability vs. accuracy." MyoElectric Controls Symposium. 2005.

Zardoshti-Kermani, Mahyar, et al. "EMG feature evaluation for movement control of upper extremity prostheses." IEEE Transactions on Rehabilitation Engineering 3.4 (1995): 324-333.

\* cited by examiner

DETERMINING INTENDED USER MOVEMENT TO CONTROL AN EXTERNAL DEVICE

RELATED APPLICATIONS

This application claims priority to U.S. Provisional Application Serial No. 62/817,785, filed Mar. 13, 2019, entitled "LOCAL ANALYSIS OF MOVEMENT EMG PATTERNS FOLLOWING PARTITIONING INTO A TRIANGULATED IRREGULAR NETWORK FOR THE PURPOSE OF DETERMINING INTENDED USER MOVEMENT DIRECTION AND MAGNITUDE IN PROSTHETIC/ROBOTIC EMG CONTROL". The entirety of this provisional application is hereby incorporated by reference for all purposes.

GOVERNMENT SUPPORT

This invention was made with U.S. government support under 5T32EB4314-20 awarded by the National Institutes of Health. The government has certain rights in this invention.

TECHNICAL FIELD

The present disclosure relates generally to determining intended user movement to control an external device (e.g., a prosthetic/robotic/virtual device) and, more specifically, to systems and methods that utilize a user-specific model of muscular activity to control the external device based on the intended user movement.

BACKGROUND

Prosthetic hands can mechanically mimic a human hand; however, most prosthetic hands are unable to match the degrees of freedom (DoF) or ease of movement achievable with a normal human hand. Commercial prosthetics do not typically exceed two DoF, and those commercial prosthetics that do exceed two DoF are expensive and face a large attrition rate with 10-35% of users abandoning prosthetic devices. This attrition rate is thought to be due to the lack of sensory feedback required for closed loop control or poor feed-forward control. Moreover, commercial devices lack the ability to continuously and proportionally control a practicable number of prosthetic movements based on user intent.

SUMMARY

The present disclosure overcomes the shortcomings of commercial prosthetics, providing systems and methods that utilize a user-specific model of muscular activity to control an external device based on intended user movement.

In an aspect, the present disclosure can include a system that utilizes a user-specific model of muscular activity to control an external device based on the intended user movement. The system includes at least one electrode configured to be located on a limb of a user; and a controller, coupled to the at least one electrode. The controller includes a non-transitory memory storing instructions; and a processor to execute the instructions stored in the memory. Upon execution of the instructions, the system can at least: receive user-specific EMG signals (including one or more EMG patterns that indicate a single movement) recorded by electrodes located on a limb of a user; decompose the user-specific EMG signals into the one or more EMG patterns in EMG feature space that indicate the single movement; and update a user-specific model of muscular activity to include the single movement and corresponding one or more primary muscle patterns based on the one or more EMG patterns in EMG feature space. The user-specific model of muscular activity can be used to control the external device based on the intended user movement determined based on muscular activity in the limb of the user.

In another aspect, the present disclosure can include a method that utilizes a user-specific model of muscular activity to control an external device based on the intended user movement. The method includes steps for updating the user-specific model of muscular activity that can be performed by a system that includes a processor. The steps include: receiving user-specific EMG signals (including one or more EMG patterns that indicate a single movement) recorded by electrodes located on a limb of a user; decomposing the user-specific EMG signals into the one or more EMG patterns in EMG feature space that indicate the single movement; and updating a user-specific model of muscular activity to include the single movement and corresponding one or more primary muscle patterns based on the one or more EMG patterns in EMG feature space. The user-specific model of muscular activity can be used to control the external device based on the intended user movement determined based on muscular activity in the limb of the user.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
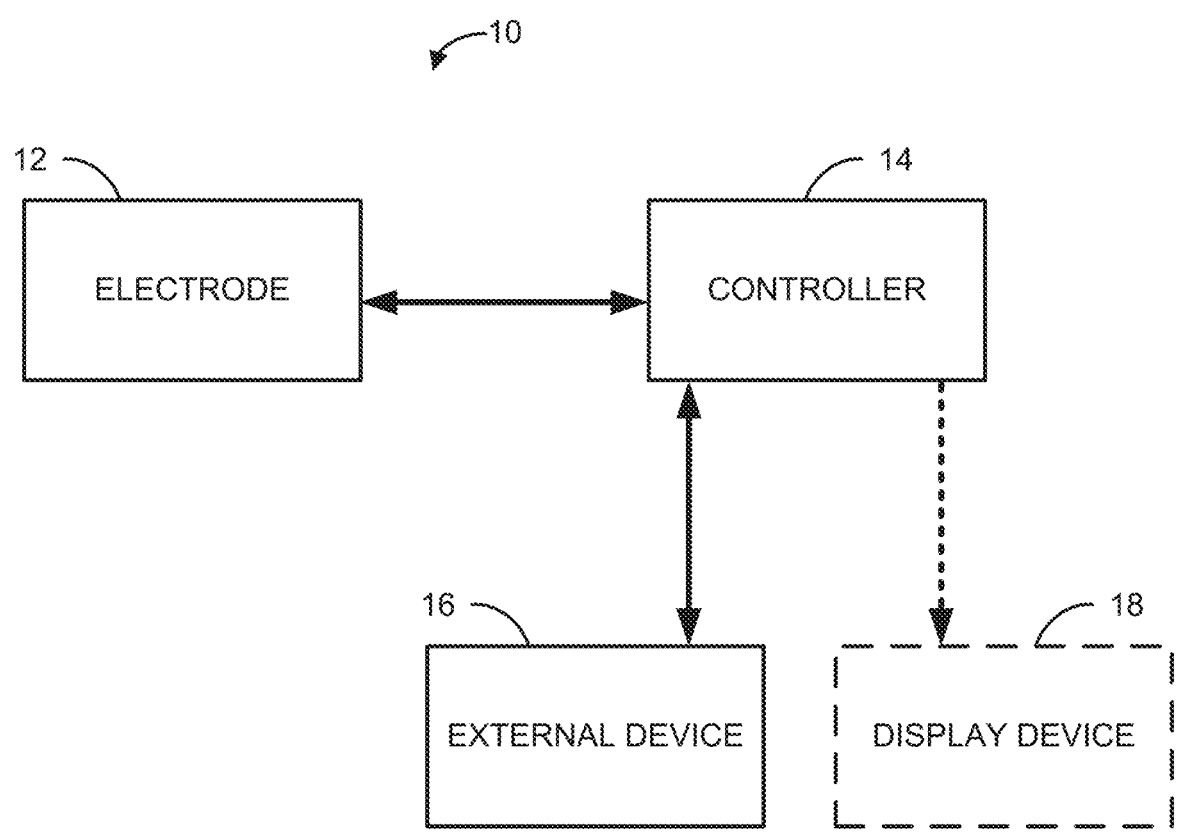
FIG. 1 is a schematic diagram showing an example of a system that can utilize a user-specific model of muscular activity to control an external device based on intended user movement, according to an aspect of the disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "external device" refers to a device or system that is not naturally part of the body of a human and can be used to enhance or return a user's senses or physical abilities. Examples of an external device can include a prosthesis or prosthetic limb, a robotic device, or a virtual system. A prosthetic limb or prosthesis refer to an artificial device that replaces a missing body part. Ideally, the prosthetic limb can be used to restore at least a portion of the normal functions of the missing body part. Prosthetic limbs can include, but are not limited to, a hand, forearm with hand, entire arm with hand, foot, lower leg with foot, or entire leg with foot. A robotic device refers to a programmable machine capable of carrying out tasks and complex series of actions. The robotic device can be attached to, located near, or located remotely from the user. A virtual system can refer to a virtual or augmented reality device where a user is interacting with a simulated or partially simulated environment.

As used herein, the term "limb" refers to a jointed, or prehensile, appendage of a human or animal body. A limb can refer to either an arm and/or hand or a leg and/or foot. The arm and hand are known as the upper limb and the leg and foot are known as the lower limb. In the case of an amputee patient a "residual limb" refers to the part of the body that remains after an amputation has been performed. In a non-limiting example, if a patient had an upper extremity amputation below the elbow, the part of the forearm that remains after the amputation is called the residual limb. In another non-limiting example, if a patient had a lower extremity amputation above the knee, the part of the thigh that remains after the amputation is called the residual limb.

As used herein, the terms "EMG signal" or "electromyogram signal" can be used interchangeably and refer to a biological signal that represents neuromuscular activities caused by a propagating wave of calcium release along muscle fibers. An EMG signal is recorded on an electromyogram by electromyography using either surface or implanted electrodes (EMG or iEMG). Electromyography is an electrodiagnostic medicine technique for evaluating and recording the electrical current generated in skeletal muscles during contraction. This signal is in the [μV] range when detected from the surface of the skin and is believed to have useful information in the 15-500 Hz range.

As used herein, the terms "intent" or "effort" refer to the user's resolve to do an action. The user's intent is determined based on EMG signals collected from the muscles in the user's limb. The EMG signals correspond to the muscular response brought on by the thought of moving the limb.

As used herein, the term "feature" refers to filtered and processed data relating to raw EMG signals. Features can include, but are not limited to, mean absolute value, enhanced mean absolute value, enhanced wavelength, slope sign change, zero crossing, waveform length, root mean square, average amplitude change, difference absolute standard deviation value, log detector, modified mean absolute value, myopulse percentage rate, simple square integral, variance of EMG, Willison Amplitude, and Maximum Fractal Length.

As used herein the term "primary muscle patterns" refers to patterns of muscle activation (e.g., including two or more muscles) corresponding to a chosen group of one or more human movements. For example, primary muscle patterns can refer to the muscle activation required for base anatomical movement such as pronation/supination, flexion/extension, eversion/inversion, abduction/adduction, medial/lateral rotation, etc. Combinations of primary muscle patterns create complex movements.

As used here in the term "synergy" refers to the activations of one or more groups of muscles, called synergist muscles, that contribute to a movement and reduce the dimensionality of muscle control. There are two types of synergist muscles true synergist muscles and helping synergist muscles. True synergist muscles are a multi-articulate muscle which causes movement at each joint it crosses and at least a second muscle which opposes the multi-articular muscle's action at at least one joint, but not at every joint. For example, hamstrings are multi-articular and produce hip extension and knee flexion, for the hamstrings to produce knee flexion without hip extension a hip flexor must act with the hamstrings in a true synergy, for the hamstrings to produce hip extension without knee flexion a knee extensor must act with the hamstrings in a true synergy. Helping synergist muscles are two or more muscles with a common action in one plane and an opposing action in another plane, wherein the action occurs around a multi-axial joint.

As used therein the term "synergy theory" refers to a theory of muscle activity which is often used to reduce EMG signal dimensionality. This is done by reinterpreting EMG activity for a movement as a linear combination of EMG generated by sub-movements called synergies. There are several formulations of the theory, one of which assumes the sub-movements to be time- invariant. As long as other assumptions of this theory are maintained - namely, that only the mean absolute value EMG signal is used, and that signals are assumed to be in 'steady state'—the theory can be invoked. Invoking this form of the theory shifts non-linear EMG space into a rather friendly, linear, synergy space. This linearity can then be used to bound the behavior of a controller on untrained EMG signals—addressing the question of controller predictability and also reducing the time needed to collect training data by allowing a structured extrapolation from collected training data.

As used herein the term "Triangulated Irregular Network" refers to a special case of a Digital Elevation Model that in this case represents at least one feature of number of EMG signals over time and consists entirely of Triangulated facets with each vertex representing a specified primary movement. A Triangulated Irregular Network utilizes original sample points, known primary movements, to constitute many overlapping triangles that cover an entire region according to a set of rules.

As used herein, the terms "user", "subject", and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

Most prosthetic hands are unable to match the degrees of freedom (DoF) achievable with a normal human hand. Commercial robotic prosthetics do not typically exceed two DoF, and a significant percentage of users abandon prosthetic devices due to the lack of sensory feedback required for closed loop control or poor feed-forward control. To combat poor feed-forward control the ideal controller is described as having many independent, functionally relevant degrees of freedom and a movement velocity proportional to user intent. Previous advances in prosthetic control have aimed to increase either movement quality or the raw number of controllable movement classes or degrees of freedom, not to correspond prosthesis movement direction and force with user intent successfully. The present disclosure creates a link between user intent and movement direction and force of either a prosthetic or a robot.

Accordingly, the present disclosure describes systems and methods that determine intended user movement based on local analysis of EMG signals to determine movement patterns to determine intended movement, which is used to control prosthetics/robotics. Local analysis utilizing the synergy framework, implanted EMG recordings, and linear interpolation combined on a triangulated irregular network of movement patterns can generate a 4D+ Simultaneous, Continuous, Intuitive, and Proportional (SCIP) controller. The systems and methods described herein provide advantages over currently available robotic prosthesis control approaches. Current approaches cannot provide the machine learning mapping from EMG features to movements with a sufficient volume of EMG data in a practical time frame and cannot provide the machine learning mapping with a corresponding 'intent' signal to match the 'EMG' signal during training. The present methods invoke the synergy theory framework to shift non-linear EMG space into a linear, synergy space. This linearity is used to bound the behavior of a controller on untrained EMG signals—addressing the issue of controller predictability and also reducing the time needed to collect training data by allowing a structured extrapolation from collected training data. Additionally, the user intent is determined based on a linear relationship with synergy magnitudes which allows proportionality in robotic prosthesis control.

III. Systems

One aspect of the present disclosure can include a system 10 (shown in FIG. 1) that can directly connect users (e.g., humans) with machines using neuromuscular interfaces. EMG signals (produced by a user) can be transformed to allow the user to manipulate an external device (e.g., a prosthetic limb, a robotic system, or a virtual system) based on the user's intended muscle movements.

The system 10 at least one electrode 12 coupled to a controller 14. The system 10 can also include an external device 16 coupled to the controller 14. In some instances, the system 10 can include a display device 18 (e.g., a graphical display, an audio display, or the like) coupled to the controller. The couplings can be connections that are wired and/or wireless. The controller 14 can be a computing device that can (1) generate/update/train a user-specific model (based on signals related to motion recorded by the at least one electrode 12) and (2) control the external device 16 based on a user intent determined with the user-specific model. The controller 14 can be external from the user or implanted alongside the one or more electrodes 12. An external controller can be part of a general computing device, such as a computer, smartphone, or tablet, or integrated with the external device or display device.

The at least one electrode 12 can be configured to be located on or within a limb of a user. For example, the at least one electrode 12 can be located on or within a muscle. The at least one electrode 12, can be, in some instances, a plurality of electrodes. The at least one electrode 12 can be surface electrodes, or implantable electrodes. The at least one electrode 12 can record a signal related to motion (e.g., one or more user-specific EMG signals) that include one or more patterns that indicate a single movement.

The external device 16 can be a prosthetic limb for an amputee user, a robotic system, or a virtual system. A prosthetic limb or prosthesis refer to an artificial device that replaces a missing body part. Ideally, the prosthetic limb can be used to restore at least a portion of the normal functions of the missing body part. Prosthetic limbs can include, but are not limited to, a hand, forearm with hand, entire arm with hand, foot, lower leg with foot, or entire leg with foot. A robotic device refers to a programmable machine capable of carrying out tasks and complex series of actions. The robotic device can be attached to, located near, or located remotely from the user. A virtual system can refer to a virtual or augmented reality where a user is interacting with a simulated or partially simulated environment. The user's real-world movements can be translated into actions in the simulated environment.

Figure 2:
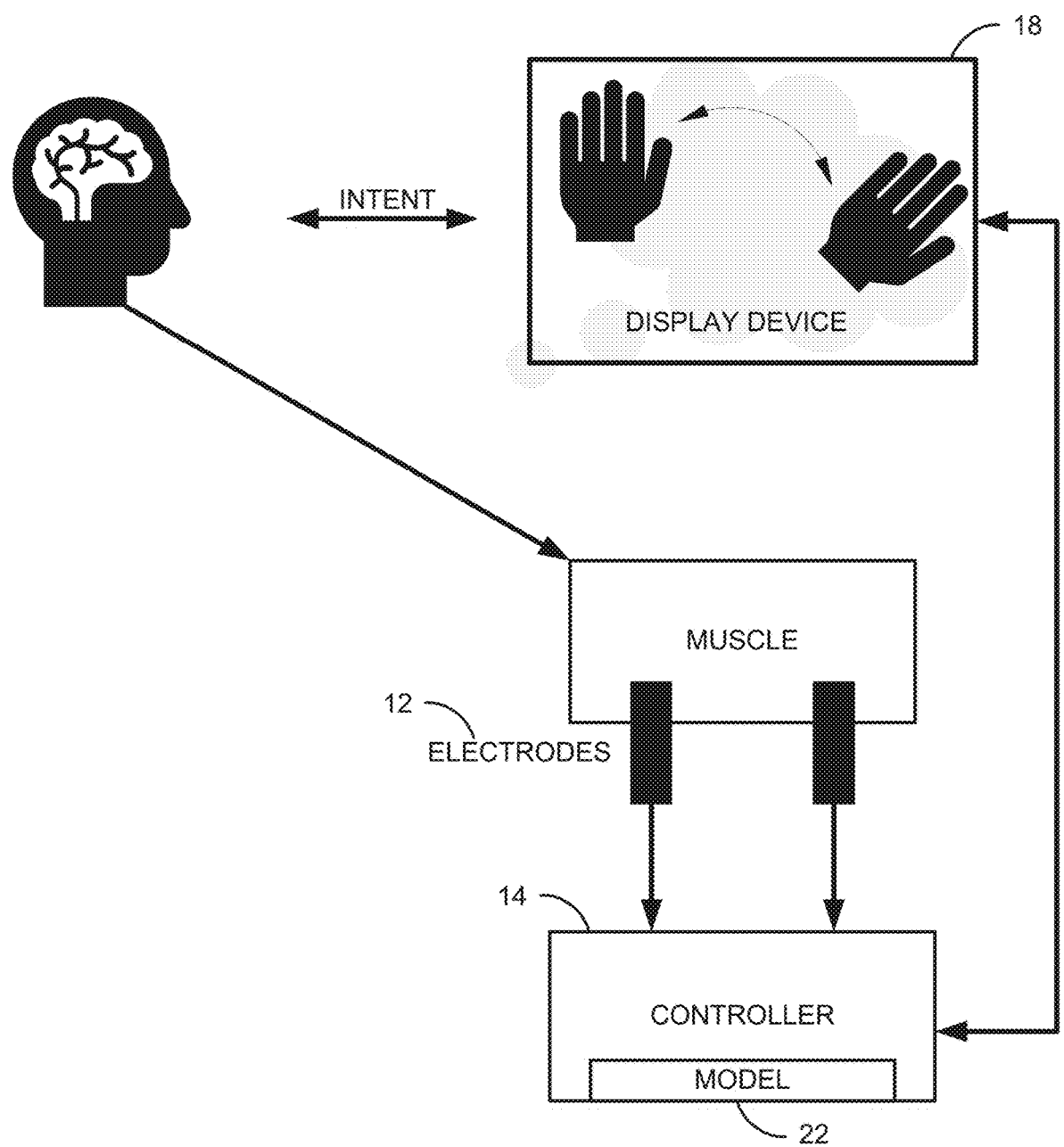
FIG. 2 is an illustration showing the system of FIG. 1 being used to train a user-generated model.

FIG. 2 shows an example of how the controller 14 generates/updates/trains the user-specific model (also referred to as "model 22"). The controller 14 can display a visualization of one or more desired movements on the display device 18. In some examples, the visualization can include a number of combinations of movements. In connection with the visualization, the display device 18 can prompt the user to move his or her limb to match the visualization. The display device 18 can be any type of display suitable for displaying text, images, graphics, and/or other visual output including, but not limited to, a standard display screen (e.g., LCD, CRT, OLED, TFT, plasma, etc.), a touch screen, a wearable display, a projection display, a head-mounted display, a holographic display, or a virtual reality display. The display device 18 can be physically attached to the controller 14 or remote from the controller 14. In this example, the user can have an intent to move a body part (e.g., an amputated hand, as illustrated) in a manner shown in the visualization. As such, the user is shown a movement or a series of movements on the display device 18 and prompted to mimic the movement(s).

One or more electrodes 12 (illustrated as two electrodes, but it will be understood that that the one or more electrodes 12 can be any number of electrodes limited only by processing ability) are implanted in at least two muscles of a limb of a user. In one example, the one or more electrodes 12 can be placed on a subject's forearm, either in a targeted approach, in a ring or grid, or by inserting targeted fine wire electrodes into muscles. In an example when the electrodes 12 are implanted in muscles in an upper limb of the patient the at least two muscles can include, but are not limited to, a Pronator, a Flexor Carpi Radialis (FCR), a Flexor Digitorum Superficialis (FDS), a Flexor Carpi Ulnaris (FCU), a Supinator, an Extensor Carpi Radialis Longus (ECRL), an Extensor Digitorum (ED) or an Extensor Carpi Ulnaris (ECU).

Figure 3:
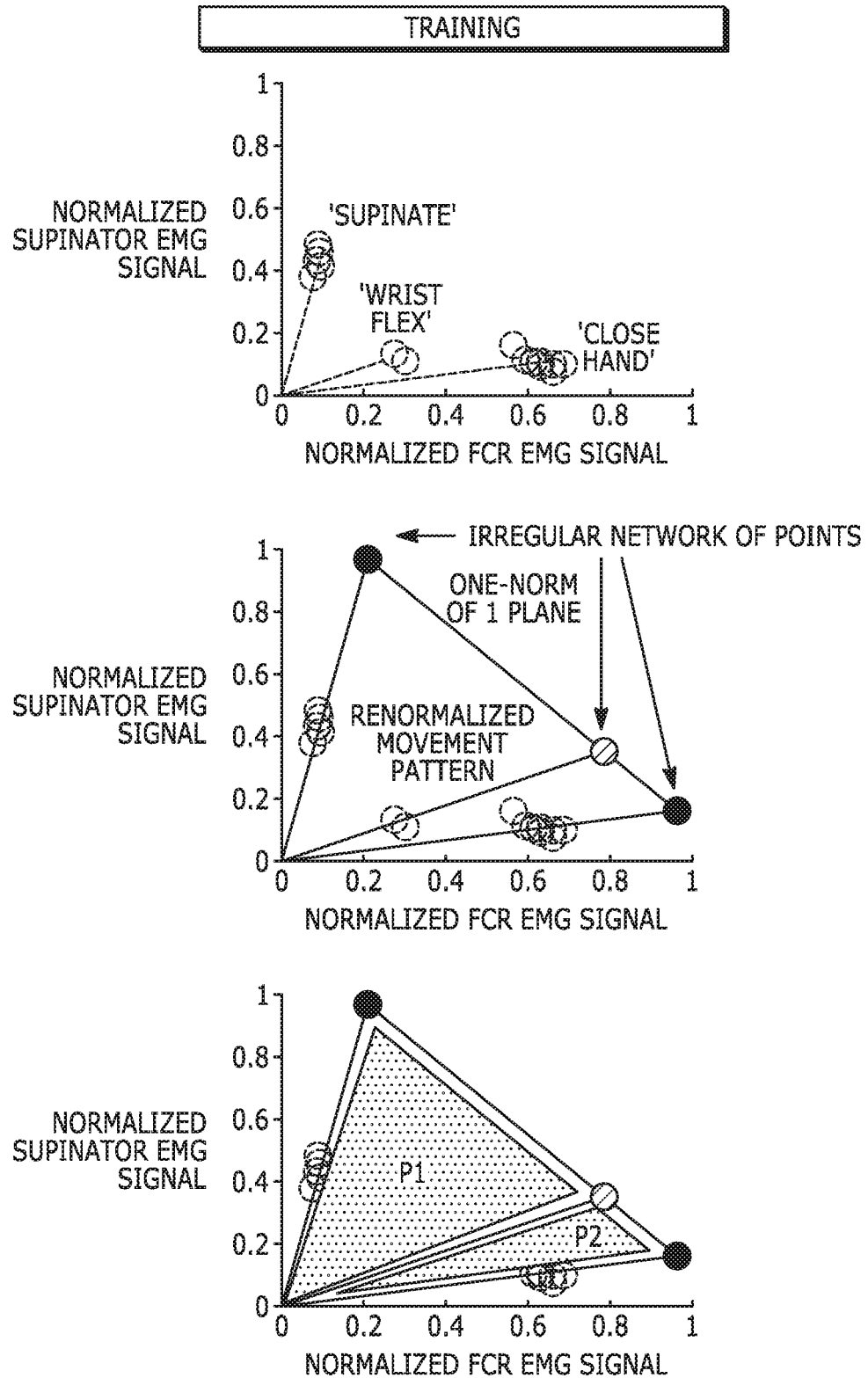
FIG. 3 is a series of graphical representations used in training the user-generated model of FIG. 2.

The user mimics/performs/attempts to perform the movement indicated on the display device 18. The one or more electrodes 12 record muscle signals related to the movement, which reflect the intent. The intention behind the movement(s) causes electrical signals to propagate through muscles and these signals are recorded as EMG signals by electrodes 12 either on or implanted in the muscles. The controller 14 receives the EMG signals and executes instructions to generate/update/train the user-specific model ("model 22"). This process can repeat for different desired movements, The model 22 can be generated, for example, by plotting normalized features of the EMG signals that correspond with known movements in one space. In FIG. 3 the plotted feature is the mean absolute value of the EMG signal. The three known movements plotted in FIG. 3 are wrist supination, wrist flexion, and hand closure. A fitting method, such as Principal Component Analysis, is used to determine primary muscle patterns for each known movement and the dominant primary muscle patters are renormalized into a co-planar arrangement of an irregular network of points. The irregular network of points is partitioned into tetrahedra of N+1 vertices by a processes such as Delaunay Triangulation which generates a Triangulated Irregular Network. The Triangulated Irregular Network is the user-specific model ("model 22").

Figure 4:
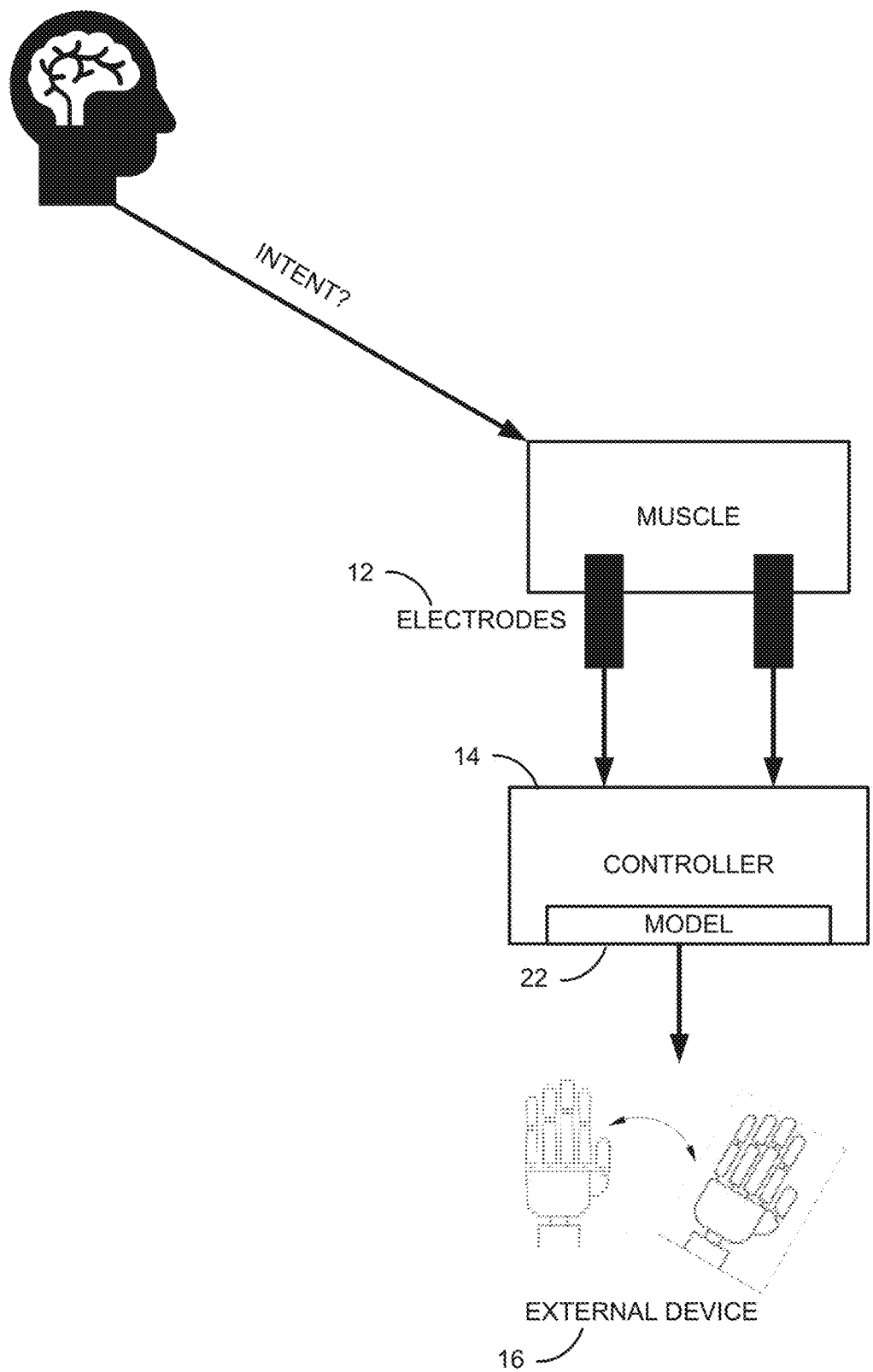
FIG. 4 is an illustration showing the system of FIG. 1 being used to control an external device based on user intent determined with the user-generated model.
Figure 5:
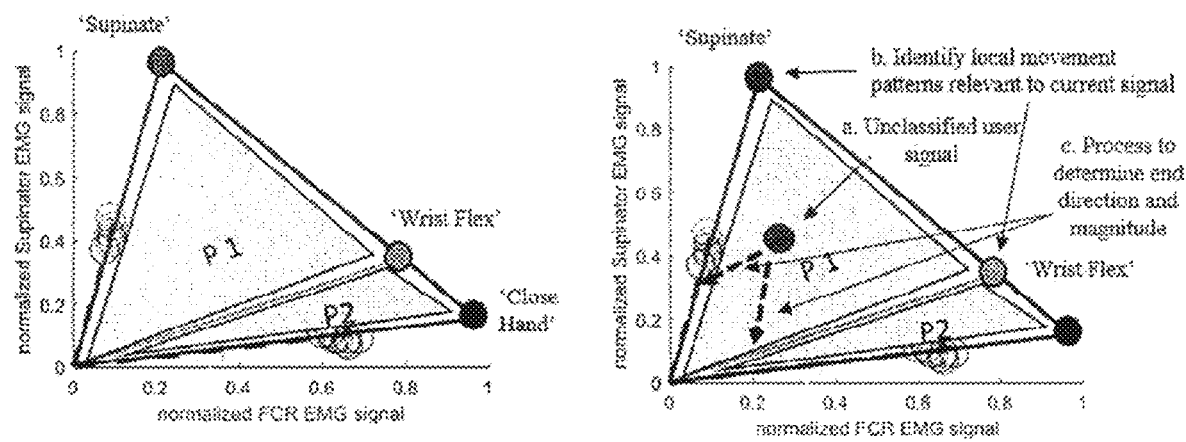
FIG. 5 is a series of graphical representations used in controlling the external device of FIG. 4.

FIG. 4 shows an example of how the controller 14 controls the external device 16 based on a user intent determined with the user-specific model ("model 22" generated/updated/trained as shown in FIGS. 2 and 3). In FIG. 4, a user formulates the intent to move a muscle, the user may or may not actually move, in any manner. The movement does not have to be a known movement used to generate the model 22. The electrodes 12 record the EMG signals of the user's muscular activation and the controller 14 receives the EMG signals. The EMG signals are then analyzed using the model 22, as shown in FIG. 5, and classified based on the known primary muscle patterns of the model 22 that make up the user's current movement. The controller 14 processes EMG signal to determine the direction and magnitude of the user's intent. The controller 14 controls movement of the external device 16 based on the processed signals that correspond to the user's intent.

Figure 6:
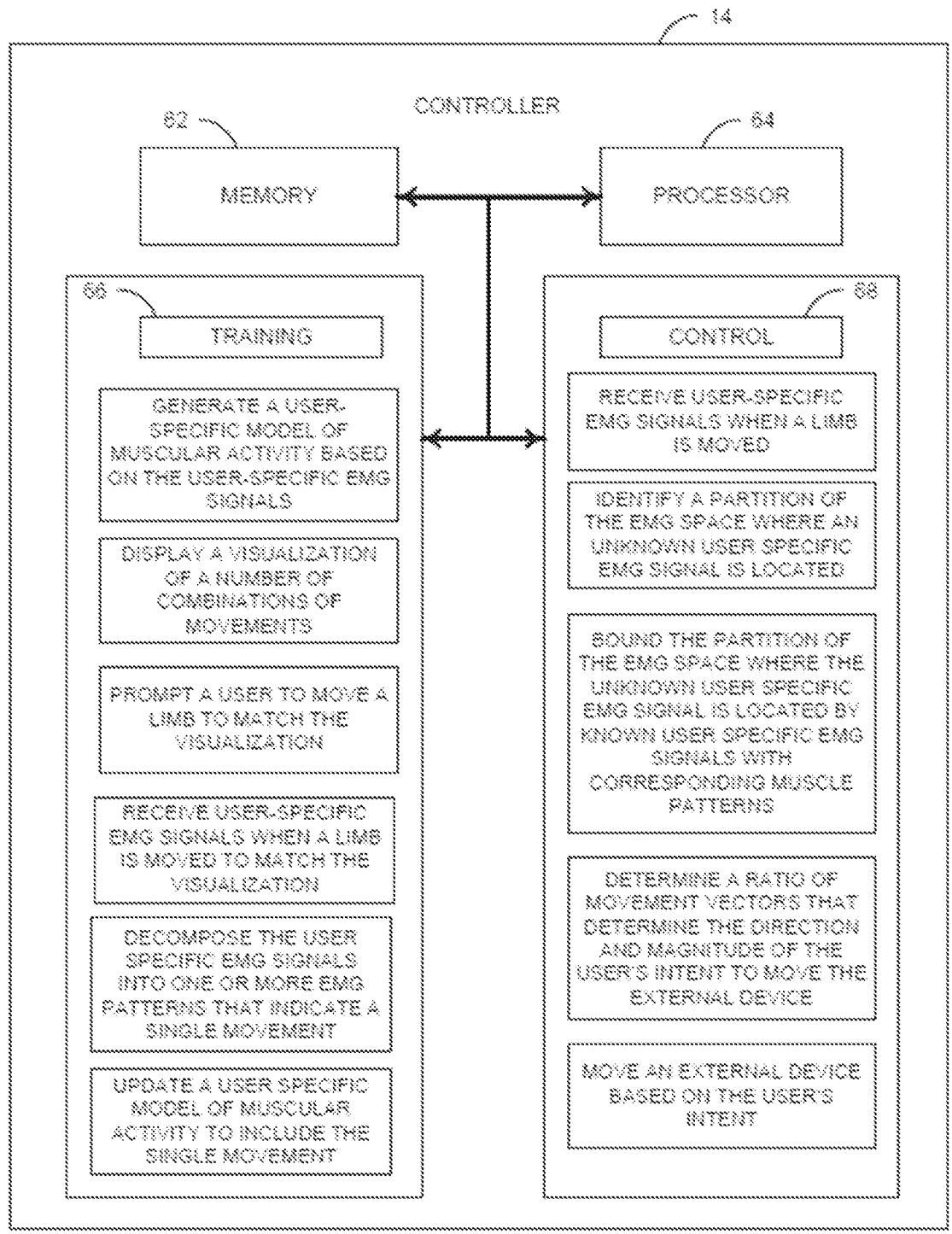
FIG. 6 is a schematic diagram showing an example of the controller of FIG. 1.

An example of the controller 14 is shown in FIG. 6. The controller includes a non-transitory memory 62 configured to store instructions and a processor 64 that can access the non-transitory memory and execute the instructions. The non-transitory memory 62 can store data, including EMG signals received from the one or more electrodes 12 and extracted features, such as mean absolute value, of the EMG signals. The controller 14 can include a wireless transmitter (not shown), which can allow communication with the one or more electrodes 12 and/or the external device 16, and optionally the display device 18. The wireless transmitter can communicate according to one or more protocols, including Bluetooth, cellular, WiFi, or the like. In some instances, the controller 14 can also include a wired connection for data transmission.

In one aspect the non-transitory memory 62 can store training instructions 66 and the processor 64 can read and execute training instructions 66. Training instructions 66 correspond with the use of the system as described above with respect to FIGS. 2 and 3. Following training instructions 66, the controller 14 can generate a user-specific model of muscular activity ("model 22") based on user-specific EMG signals. The controller 14 instructs the display device 18 to display a visualization of a number of combinations of movements and to prompt a user to move a specific limb to match the visualization. The controller 14 receives user-specific EMG signals recorded by the electrodes 12 during the user's movement. The user-specific EMG signals can comprise one or more EMG patterns that indicate a single movement. The controller 14 can decompose the user-specific EMG signals into the one or more EMG patterns in EMG feature space that indicate the single movement and update the user-specific model of muscular activity ("model 22") to include the single movement and corresponding one or more primary muscle patterns based on the one or more EMG patterns in EMG feature space.

The user-specific model is updated by the following instructions, not shown in FIG. 6. The controller 14 extracts a feature from each the one or more EMG patterns in the EMG feature space that indicate the single movement, wherein each of the user specific EMG signals is recorded by a different electrode. The feature is preferably a mean absolute value. The controller 14 determines, by a fitting method, the one or more primary muscle patterns for the feature. The fitting method can be, for example, Principal Component Analysis or Non-Negative Matrix Factorization. The controller 14 generates the EMG feature space based on the feature extracted for the single movement. The controller 14 partitions the EMG feature space into a tetrahedra of N+1 vertices, the partitioning can be done by Delaunay Triangulation which divides the EMG feature space into the tetrahedra with a maximized minimum internal angle. The controller 14 generates a Triangulated Irregular Network based on the tetrahedral of N+1 vertices. The Triangulated Irregular Network corresponds to the user-specific model of muscular activity (model 22) that can then be used to control an external device.

In another aspect, the non-transitory memory 62 can store control instructions 68 and the processor 64 can read and execute the control instructions 68. Control instructions 68 correspond with the use of the system as described above with respect to FIGS. 4 and 5. The controller 14 can predict an intent of the user to move the external device based on the user-specific model of muscular activity (model 22) when the processor 64 executes the following instructions. The controller 14 identifies a partition of the EMG feature space where the unknown EMG signal is located. The controller 14 bounds the partition of the EMG feature space where the unknown EMG signal is located by known single movements with a corresponding one or more primary muscle patterns. The controller 14 determines a ratio of movement vectors that should be combined to determine the direction and the magnitude of the intent of the user to move the external device 16. The ratio of movement vectors corresponds to the unknown EMG signal. Thereby, a user can successfully have simultaneous, continuous, intuitive, and proportional control of an external device 16 in real-time, or near-real time, based on the user's intention to move a limb. A controller 14 is simultaneous if users can move the external device 16 in real time, or near-real time. A controller 14 is continuous if it combines movements in any ratio and does not rely on only a set group of ratios. A controller 14 is intuitive if the movements of the external device 16 match the direction and magnitude of the user's intention to move. A controller 14 is proportional if users have the ability to modulate the speed with which the external device 16 executes corresponding movements.

IV. Methods

Another aspect of the present disclosure can include methods 70, 80, 90, and 1000 as shown in FIGS. 7, 8, 9, and 10 for generating/updating/training a user-generated model of intent and/or controlling an external device based on user intent determined using the user-generated model. For example, the user generated model can be used for determining intended user movement to control an external device 16 (e.g., a prosthetic/robotic/virtual device).

The methods 70, 80, 90, and 1000 are illustrated as a process flow diagram with flow chart illustrations. For purposes of simplicity, the methods are shown and described as being executed serially; however, it is to be understood and appreciated that the present disclosure is not limited by the illustrated order, as some steps could occur in different orders and/or concurrently with other steps shown and described herein. Moreover, not all illustrated aspects may be required to implement the methods.

The methods 70, 80, 90, and 1000 can be executed by hardware—for example, the methods 70, 80, 90, and 1000 can be performed primarily by the controller 14 of the system 10 of FIG. 1. One or more hardware elements of the controller 14 of system 10 can execute software routines to implement at least a portion of each of the methods. Additionally, one or more elements of the controller 14 of system 10 can include a non-transitory memory 62 storing the software routines and one or more processors 64 to execute the software routines corresponding to at least the portion of the methods. Other components (external device 16, display device 18, etc.) of the system 10 of FIG. 1 may also be used to facilitate the methods.

Figure 7:
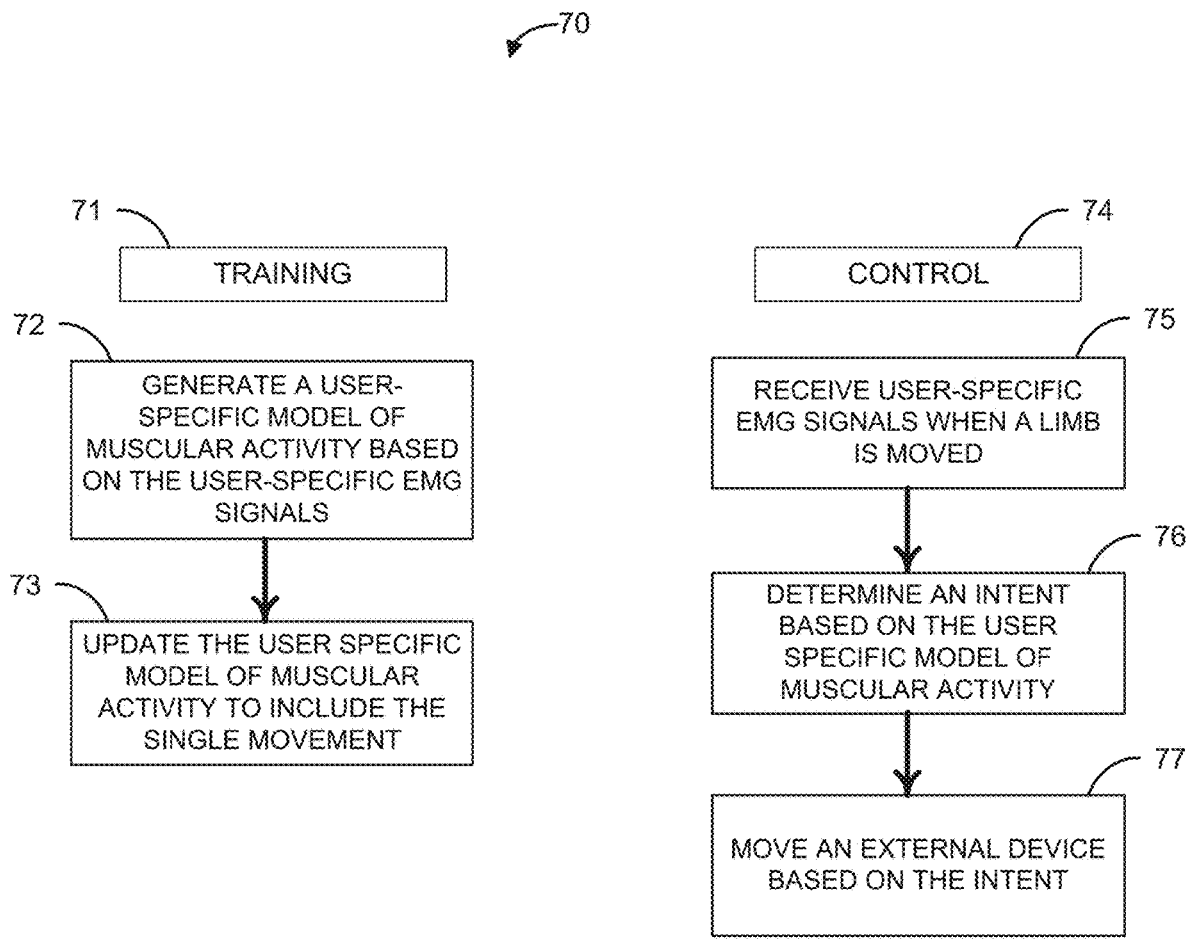
FIGS. 7-10 are process flows diagram showing methods for generating/updating/training a user-generated model of intent and/or controlling an external device based on user intent determined using the user-generated model, according to another aspect of the disclosure.

Referring now to FIG. 7, the method 70 for training a user-specific model and controlling an external device with the user-specific model is illustrated in two parts, a training method 71 and a control method 74. As part of the training method 71, the controller generates a user specific model of muscular activity based on user-specific EMG signals at 72. Known user-specific EMG signals are recorded by electrodes configured on the user and received by the controller to generate the user-specific model of muscular activity. At 73 the controller updates the user-specific model of muscular activity to include a user movement made during training. When training the user-specific model, generating and updating the user-specific model can further include the following steps, not shown in FIG. 7. The display device visualizes a number of combinations of movements to the user and the display device prompts the user to move his or her limb to match the visualization. The user moves his or her limb to match the visualization, thereby creating known movements. In one example, where the limb is an upper limb the movements can comprise, but are not limited to, wrist flexion/extension, wrist pronation/supination, D2 flexion/extension, thumb palmer movement, thumb lateral movement, wrist radial/ulnar deviation, and D3-D5 flexion/extension.

As part of the control method 74, the controller receives, at 75, user-specific EMG signals when a user moves a limb. At 76 the controller determines the user's intent based on the user-specific model of muscular activity. In response to determining the user's intent at 77 the controller moves an external device.

Figure 8:
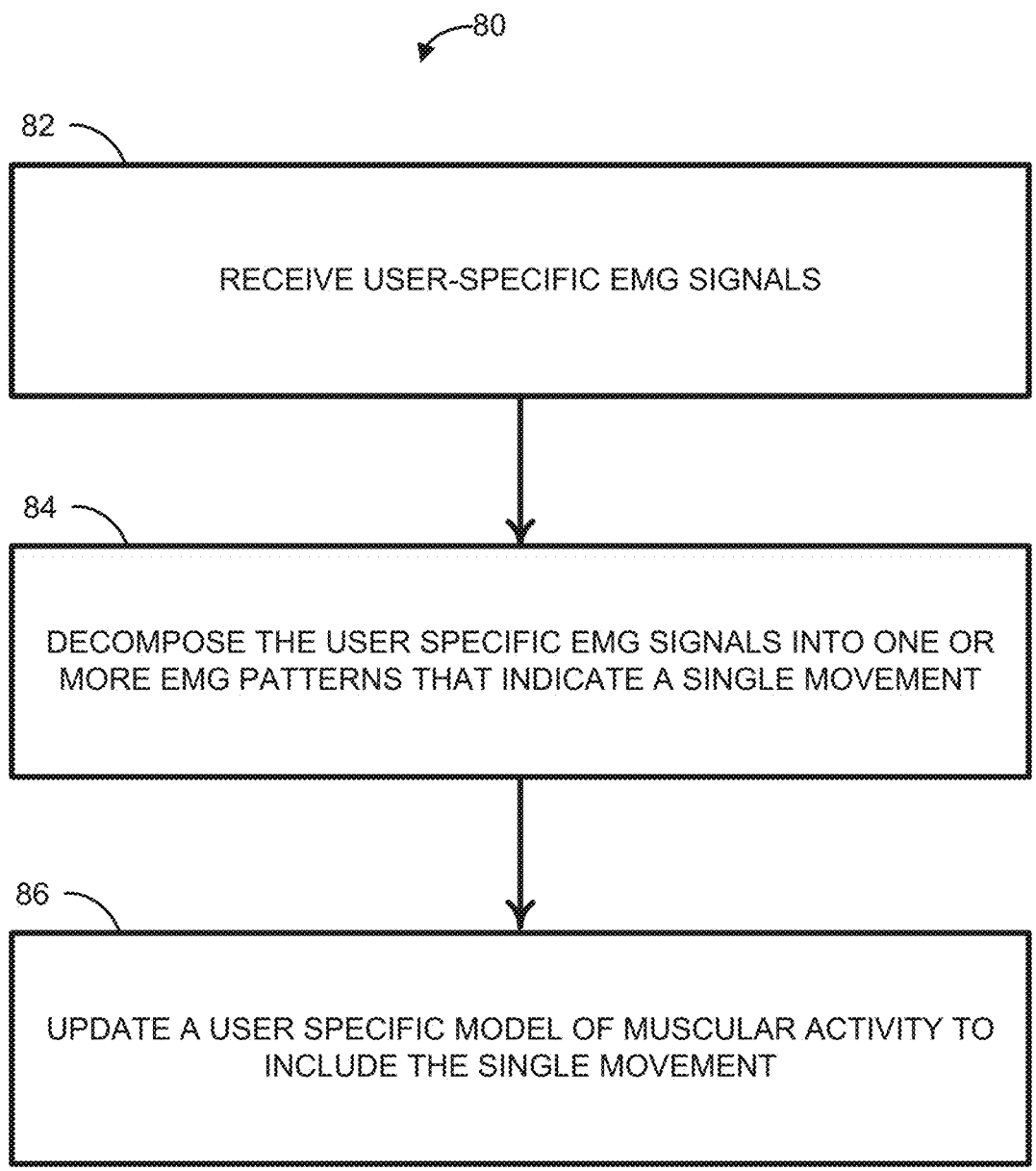

Referring now to FIG. 8, illustrated is a method 80 for updating the model, which can be used for determining intended user movement to control an external device. At 82, user-specific EMG signals recorded by electrodes are received by the controller. The user-specific EMG signals comprise one or more EMG patterns that indicate a single movement. The electrodes are located on a limb of a user and are preferably implanted into at least two muscles of the limb. If the limb is an upper limb then the at least two muscles can comprise, but are not limited to, the Pronator, Flexor Carpi Radialis (FCR), Flexor Digitorum Superficialis (FDS), Flexor Carpi Ulnaris (FCU), Supinator, Extensor Carpi Radialis Longus (ECRL), Extensor Digitorum (ED), or Extensor Carpi Ulnaris (ECU) muscles. At 84, the user-specific EMG signals are decomposed by the controller into the one or more EMG patterns in EMG feature space that indicate the single movement. At 86, a user-specific model of muscular activity is updated to include the single movement and corresponding one or more primary muscle patterns based on the one or more EMG patterns in EMG feature space. The user-specific model of muscular activity can be used to control an external device based on muscular activity in the limb of the user. The external device can be one of a prosthetic limb, a robotic system, or a virtual system.

Figure 9:
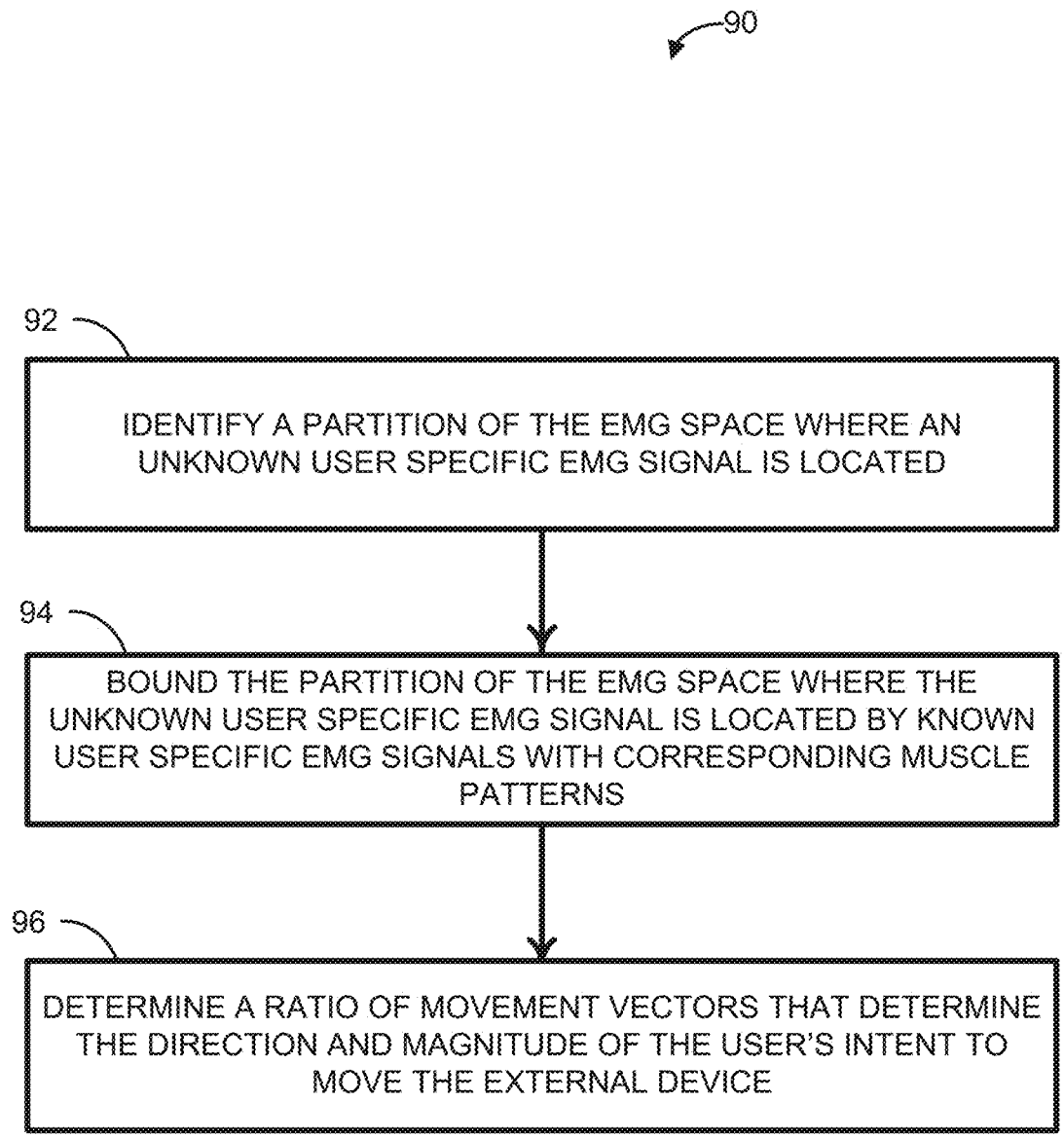

Referring now to FIG. 9, the method 90 illustrates how the external device can be controlled based on a predicted intent of the user to move the external device by utilizing the user-specific model of muscular activity when the controller receives an unknown EMG signal from the user. At 92 the controller identifies a partition of the EMG feature space where the unknown EMG signal is located. At 94 the controller bounds the partition of EMG feature space where the unknown EMG signal is located by known single movements with a corresponding one or more primary muscle patterns. At 96 the controller determines a ratio of movement vectors that determine the direction and magnitude of the user's intent to move the external device. The ratio of movement vectors corresponds to the unknown EMG signal and is used by the controller to move the external device.

Figure 10:
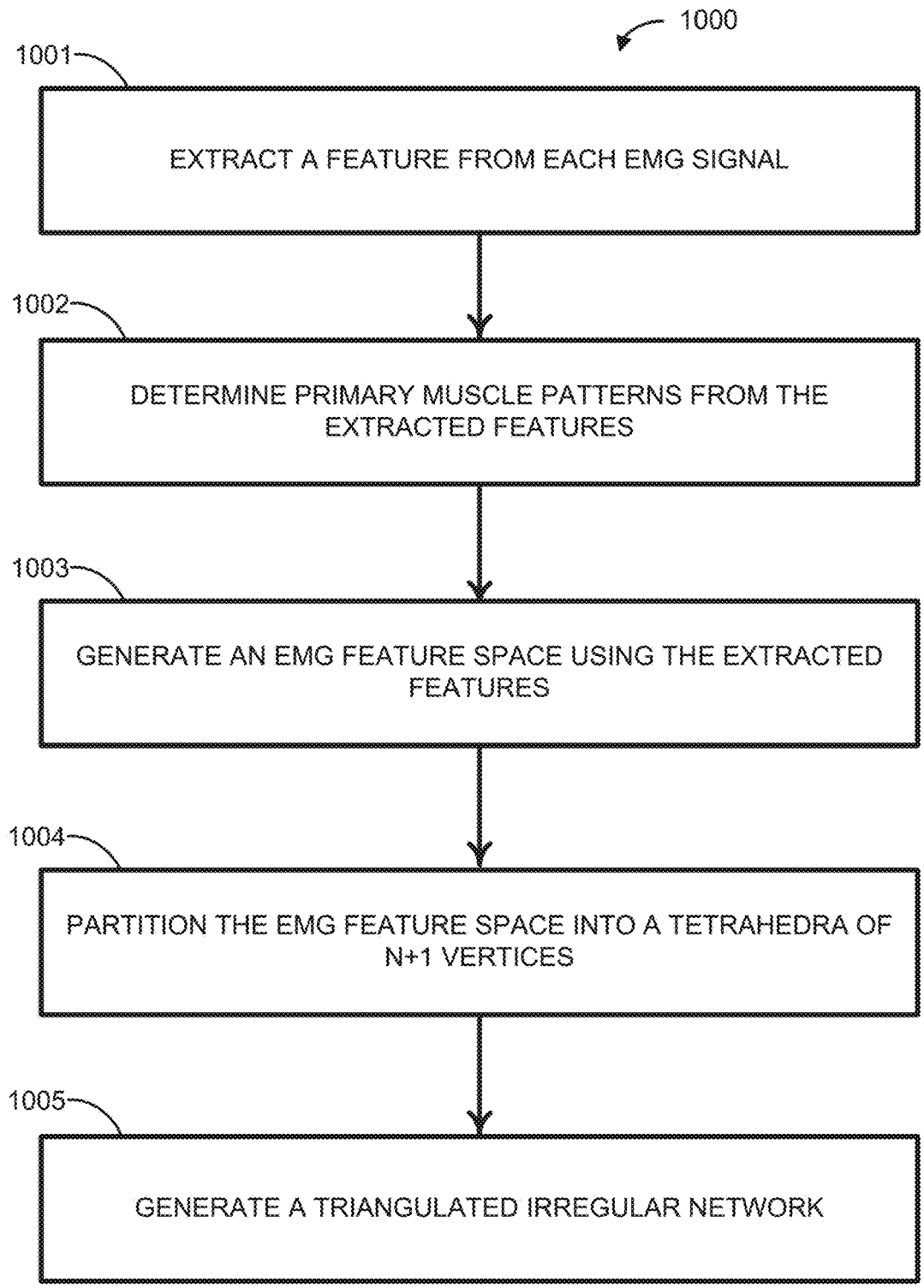

Referring now to FIG. 10, the method 1000 illustrates further steps involved in decomposing the user specific EMG signals into one or more EMG patterns that indicate a single movement can include the following steps. At 1001 the controller extracts a feature from each of the one or more EMG patterns into EMG features space that indicates the single movement. Each of the user-specific EMG signals can be recorded by a different electrode. The feature can preferably be a mean absolute value. At 1002, the controller determines, by a fitting method, the one or more primary muscle patterns from the extracted feature. The fitting method can preferably be a Principal Component Analysis. The one or more primary muscle patterns can in one aspect be fixed ratios of muscle synergies. At 1003, the controller generates EMG feature space based on the feature extracted for the single movement. At 1004, the controller partitions the EMG feature space into a tetrahedra of N+1 vertices. Preferably, the controller uses Delaunay Triangulation to partition the EMG feature space and divide it into a tetrahedra with a maximized minimum internal angle. At 1005, the controller generates a Triangulated Irregular Network based on the tetrahedra of N+1 vertices. The Triangulated Irregular Network corresponds to the user-specific model of muscular activity.

V. Experimental

The following example shows the control of a prosthetic hand based on user intent determined based on a user-specific model. The following example is for the purpose of illustration only is not intended to limit the scope of the appended claims.

Methods

Two amputee subjects participated in the study. Both were previously implanted with 8 pairs of intramuscular IM-MES EMG recording electrodes and 2 nerve cuff electrodes, accessed through percutaneous leads. After recording training data, a controller incorporating the synergy framework was developed and evaluated through a posture-matching task.

Data and Training

Two human subjects had their Pronator, Flexor Carpi Radialis (FCR), Flexor Digitorum Superficialis (FDS), Flexor Carpi Ulnaris (FCU), Supinator, Extensor Carpi Radialis Longus (ECRL), Extensor Digitorum (ED) and Extensor Carpi Ulnaris (ECU) muscles on their residual limb implanted with IM-MES EMG electrodes. Two intramuscular electrode channels on S2, located in the Pronator and ECU, began showing considerable noise 11- and 17-months post-implant so were excluded from use. Training data was recorded 23 months post-implant for S1, and 12 months post-implant for S2.

Training data acquisition was guided by a Matlab-interfaced computer visualization. The visualization shows two hands, whose joints can be controlled in real time through a Matlab/Simulink interface. Hands can be individually configured to display a target posture, a hand controllable by user EMG, or a hand linked to kinematic sensors. Training involved combinations of seven movements. Three 'fundamental' movements were included: wrist flexion/extension, wrist pronation/supination, and D2 flexion/extension. For the fourth degree of freedom, four 'new' movements were evaluated: a thumb palmar movement, a thumb lateral movement, wrist radial/ulnar deviation, and D3-5 flexion/extension. For each set, subjects were prompted by the visualization to move their phantom limb in all single and paired combinations of the four movements, while mirroring the action with their intact limb.

Subjects were given 2 seconds to interpret a target posture, 2 seconds to contract, as indicated by a change in screen color, and then a 1 second pause before the subsequent posture was presented. Training was done in batches of 5-10 movements, with the order within each batch randomized and each batch repeated five times. Movements were collected first as single directions, then in pairs, to minimize confusion. To further reduce confusion and remain on time, a researcher repeated this exercise while sitting next to the subject. Subsequent batches were started when subjects indicated that they were ready to proceed.

Figure 11:
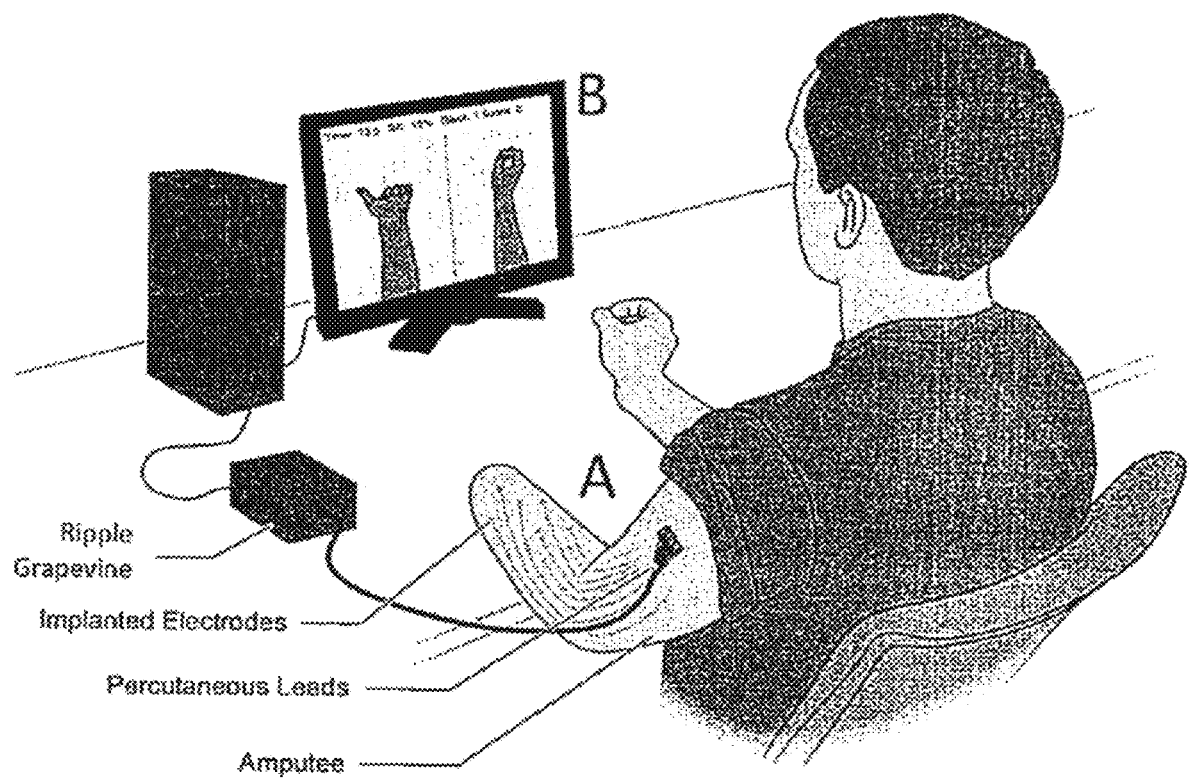
FIG. 11 is a graphical representation of an experimental setup for training a user-generated model.

The above described training and testing set up is shown in FIG. 11. As shown in FIG. lithe Ripple Grapevine system was used to collect EMG activity at 2 kHz with 15-350 Hz filters. The only EMG feature collected was the mean absolute value over a 200 ms window updated every 50 ms.

Controller

The synergy framework provides a promising structure around which to build an algorithm, due to its agnosticism towards movement sampling, its predictable linear structure, and the option to implement controller proportionality without relying on global EMG levels. To engage the synergy framework, incoming EMG signals must be limited to only the mean absolute value feature. This reduces the amount of information available but allows the use of the synergy framework's assumptions. The trade-off is viable largely due to iEMG's improved signal quality.

Engaging the framework gives two strong assumptions to build around. First, it posits that as a user's level of effort changes for a particular movement, the pattern of muscle activity does not change, only its magnitude. This means that scaling a steady state EMG signal should not change the prosthesis direction. Second, the framework declares that any movement is some linear combination of sub-movements. A corollary of this statement is that by any movement can also be described as a linear combination of other, surrounding, movements. These two statements sufficiently describe a linear space, and linear interpolation is therefore a natural choice in this environment.

Direct linear interpolation over all user movement patterns is not reasonable as the number of knowns (in this case 32 muscle patterns) exceeds the number of unknowns (8 EMG signals). This can be, and frequently has in other applications, been resolved by partitioning space into chunks and interpolating locally. To do this, each movement pattern is first renormalized to a one-norm of '1', pushing all movement patterns onto the same plane, then partition space using Delaunay triangulation, which divides space into tetrahedra while maximizing the minimum internal angle. The renormalization ensures that each of these partitions has a vertex at the origin and extend outwards, just as the synergy framework expects. The triangulated EMG signals are not located on a grid, and so the resulting structure is referred to as a Triangulated Irregular Network.

Figure 12:
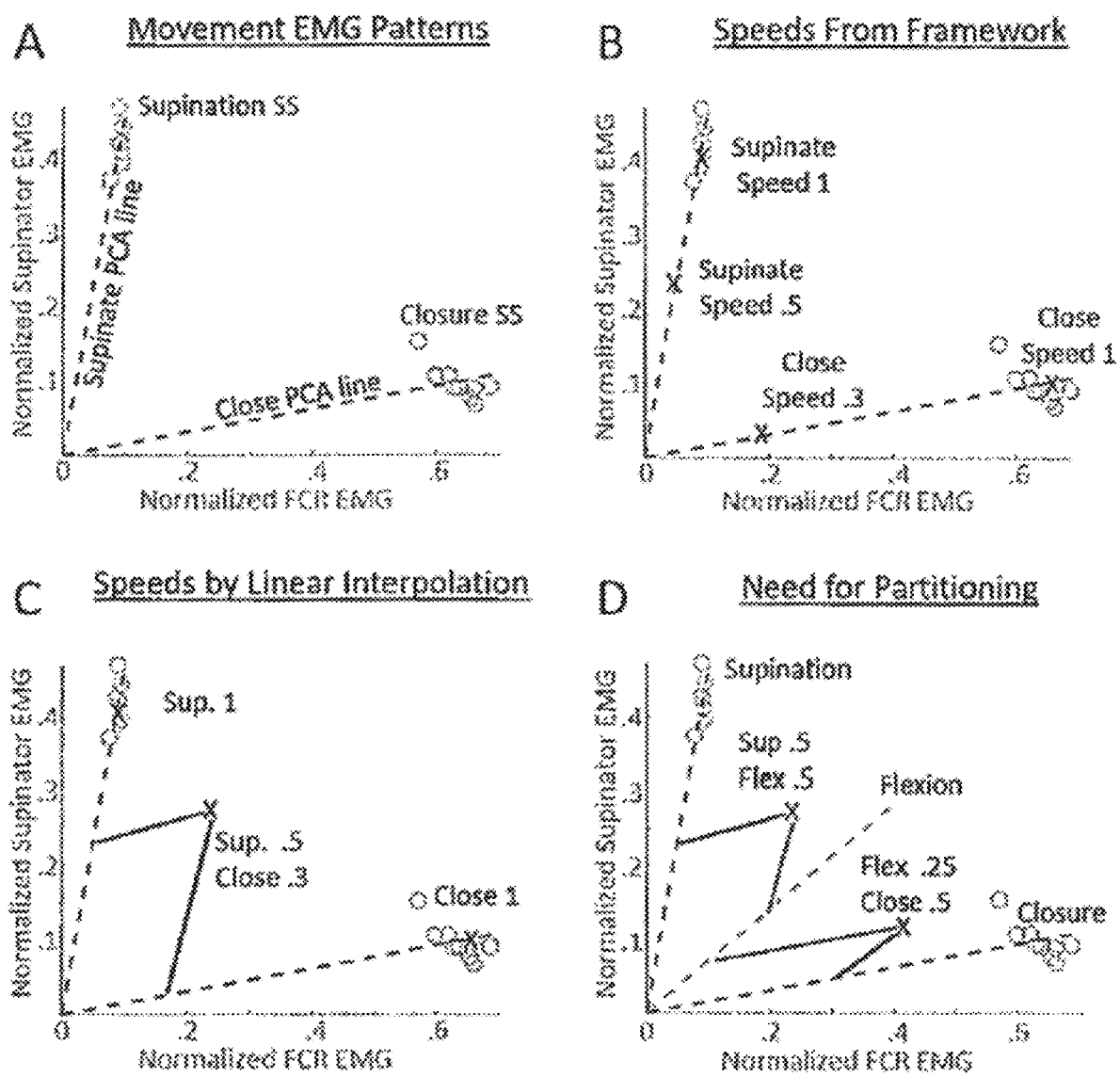
FIG. 12 is a series of graphical representations used to generate a Triangulated Irregular Network when the primary muscle patterns are supination, flexion, and hand closure and determining unknown movements within the primary muscle pattern.

For a novel EMG signal Mu, the process is therefore:
I. Identify which partition of EMG feature space the unknown signal $M_u$ is in. The partition is bounded by known EMG signals $\{M_1, M_2, \ldots M_8\}$ with corresponding movement classes $\{C_1, C_2, \ldots C_s\}$.
II. Find Coefficients $\{K_1, K_2, \ldots K_s\}$ such that $M_u = K_1 M_1 + K_2 M_2 \ldots K_8 M_8$, $K_1 + K_2 + \ldots + K_8 = 1$, and min $\{K_1, K_2, \ldots K_s\} >= 0$
III. The direction and magnitude of intent are given by $K_1 C_1 + K_2 C_2 \ldots + K_s C_s$ The process is graphically represented in the series of graphs of FIG. 12. Graph A shows the movement EMG patterns and magnitudes as found by a least distance fit of steady state data for each movement, such as Principle Component Analysis. Graph B shows the movement EMG patterns as fixed ratios of synergies with the synergy magnitudes scaled linearly with user effort. As a user exerts more or less effort or speed, the corresponding EMG signal must linearly shift further or closer to the zero point on the movement EMG pattern line. Graph C shows an unknown movement EMG pattern described as a linear combination of known movement EMG patterns. In a corollary of Graph B, any movement EMG pattern can be shown as a linear combination of other nearby, surrounding movement EMG patterns. This formulation of the synergy framework naturally encourages linear interpolation. Graph D shows the need for partitioning as the number of movement EMG patterns recorded (32) exceeds the number of EMG signals (8). When the number of movement EMG patters recorded exceeds the number of EMG signals interpolation must be done locally. This is done by treating each muscle pattern as a vertex and partitioning the space with Delaunay triangulation.

Velocity Curve

Figure 13:
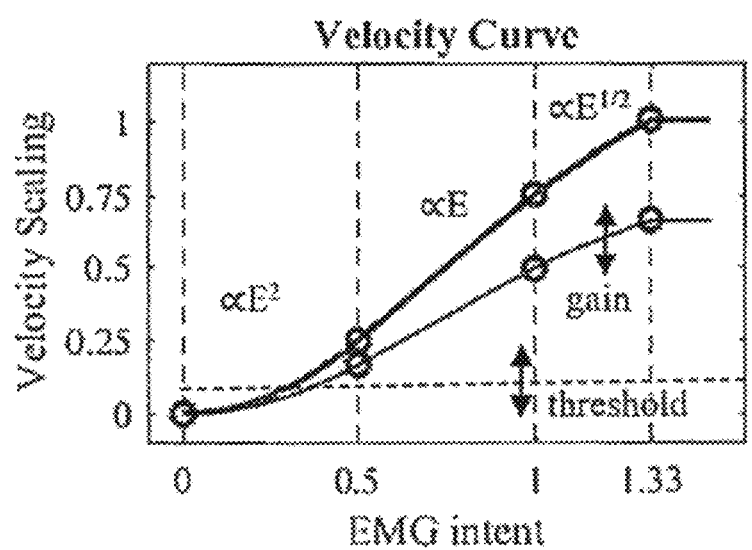
FIG. 13 is a graphical representation of a velocity curve.

The proposed controller does not directly find a value for hand velocity—instead estimating the level of user effort. Rather than simply relate effort in a 1:1 manner to hand velocity, it was chosen to mimic the physiologic behavior. As the number of muscle fibers recruited- and hence the magnitude of the EMG signal—grows, the rate at which force is exerted increases. Once higher levels of activity are reached and certain fibers are 'maxed out', the force exerted drops off. The velocity curve as shown in FIG. 13 exemplifies the translation from the subject's intended effort to the velocity a hand would move.

The medium level of effort exerted by subjects in training was given a nominal effort level of '1'. Effort values below 0.5 were set to correspond to only 25% of movement velocity in an exponential manner, then to smoothly transition to linearly grow until an EMG level of '1' was observed. Higher EMG levels were smoothly square-rooted, until a hard cap was reached at 33% above observed user levels. This mapping should make smaller movements easier, while discouraging fatiguing movements by curtailing their effectiveness. Prior to online controller evaluation, gains and thresholds per degree of freedom were adjusted to user preference. Thresholds were typically in the 0.05-0.1 range, negating unintentional drift.

Controller Evaluation

To evaluate the prosthetic controller, subjects were asked to match 80 postures in a virtual reality environment in 5 batches of 16, to an accuracy of 15% range-of-motion for each degree of freedom. To match a target, subjects had to remain within the 15% target range for a continuous second. Postures were presented in a quasi-random order, with no posture being within 30% of the previous target nor within 15% of an edge of a range-of-motion. Targets timed out after 30 seconds, and cases where the next target was immediately within range of the virtual hand were excluded from analysis. Subjects were given as much time to rest as they wanted between batches.

In 4D, the 80 postures included transitions in all simultaneous and individual non-rest combinations of 4 degrees of freedom in a quasi-random order. In 3D, the targets included 3 repetitions of all 27 non-rest combinations of degrees of freedom, and two additional targets which were excluded from analysis. These target sets span the expected movement space without burdening the user with extensive testing times but are limited to very few repetitions of each gross movement.

Targets were generated as 80 target conditions. Each target condition was a binary 1×4 vector indicating an increase/decrease/no change in each of 4 degrees of freedom, all placed in a list L. The virtual hand's posture began in a neutral state, which was the mean of all ranges of motion. If a posture could be generated which would create a change in posture as described by the topmost element of L, while being 30% range of motion (ROM) from the current posture and 15% ROM from movement limits in all applicable degrees of freedom, a posture was randomly generated within those conditions. That element in 'L' was then marked as 'satisfied', and the process repeated for the next row in L. It frequently occurred that a subsequent posture could not be generated in such a manner—i.e., a generated posture would be outside the virtual hand's ROM. In this case, all 'unsatisfied' elements in L were circularly shifted until a useable row of L was found—the aim was to attempt to maintain the randomly generated order, while still generating useable targets. In the case that no subsequent condition could be satisfied, the previous row of L' was marked 'unsatisfied', all 'unsatisfied' elements were circularly shifted, and the process repeated. In this manner, target order was generated randomly, but targets were then re-ordered to maintain target limits.

The 3D and 4D target matching tasks were also repeated with electrogoniometer recordings of the subjects' intact limb. In the 4D case, thumb flexion/extension was used as the fourth degree of freedom.

The most all-encompassing metric is 'time to match', which is the time to reach a target prior to the 1 second hold time. Given the spread in target difficulties varying by the number of degrees of freedom involved, most metrics are presented in a pairwise comparison to the intact limb's performance. The metrics are likely to be largely determined by targets involving a paired movement with a smaller emphasis on single-direction or very complicated motions, simply due to the distribution of gross movements examined.

Results

The default controller was trained on single and paired movements, and the movement patterns for each motion were determined by taking the average of 3 of 5 steady state EMG patterns, excluding the two outliers. Not all controllers proved to be viable for both subjects.

Figure 14:
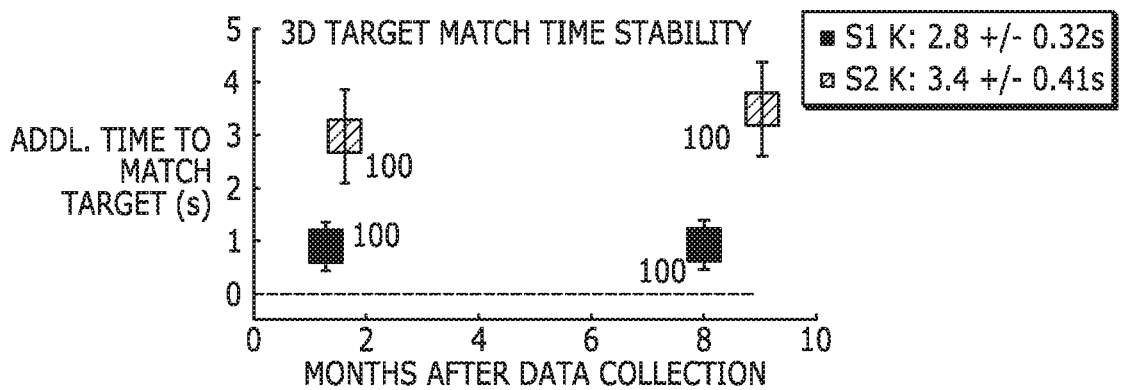
FIG. 14 is a graphical representation showing experimental results including target match time stability and path efficiency.
Figure 14:
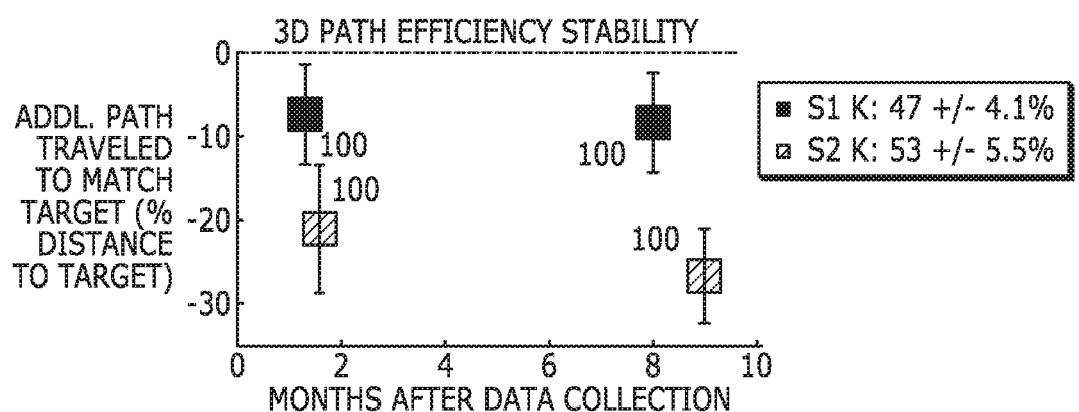
Figure 14:
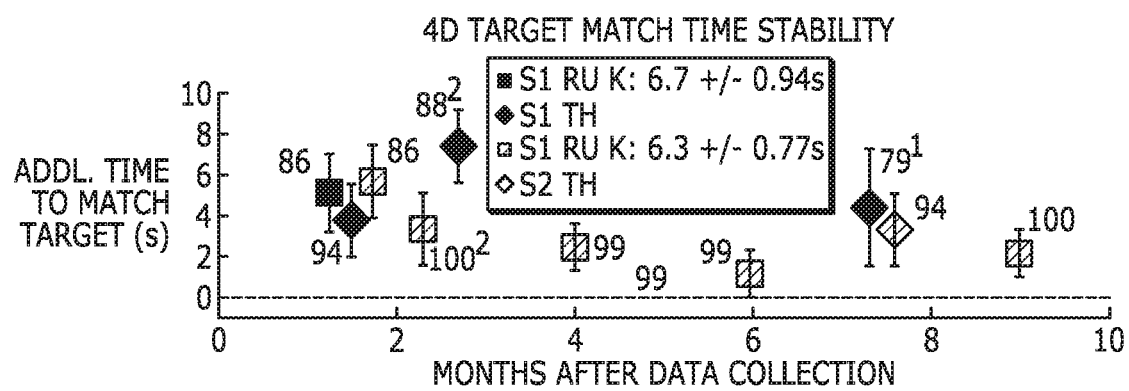
Figure 14:
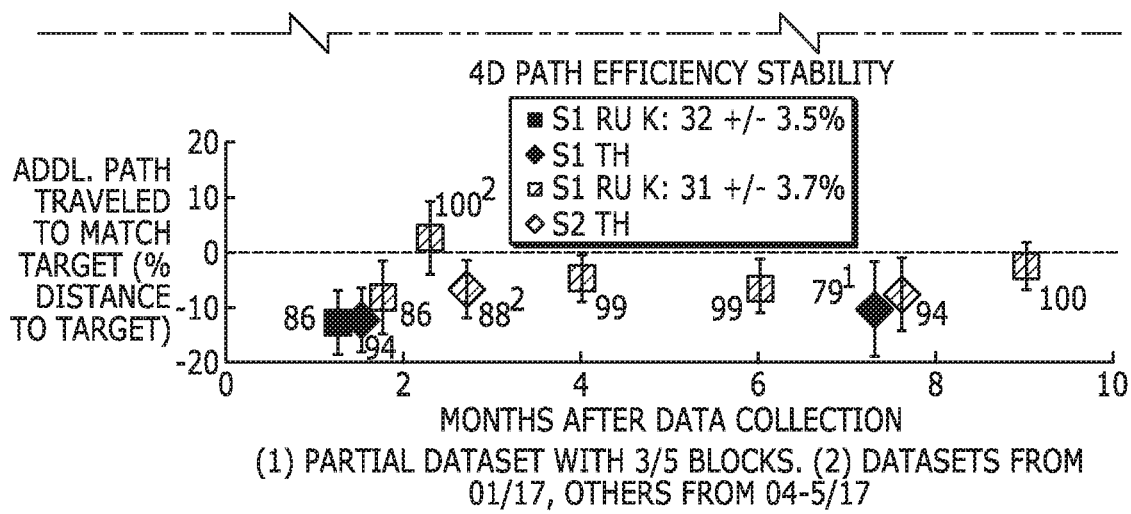
Figure 14:
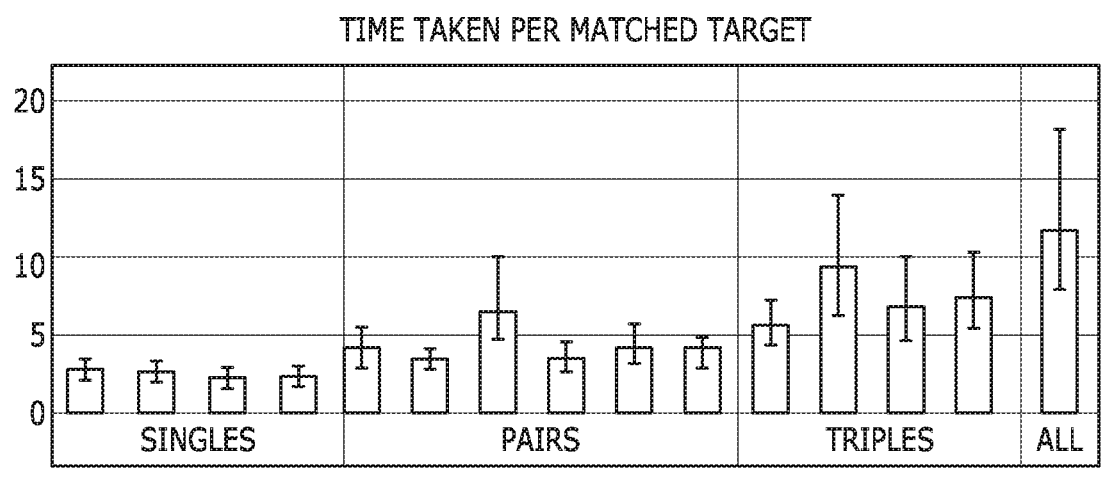
Figure 14:
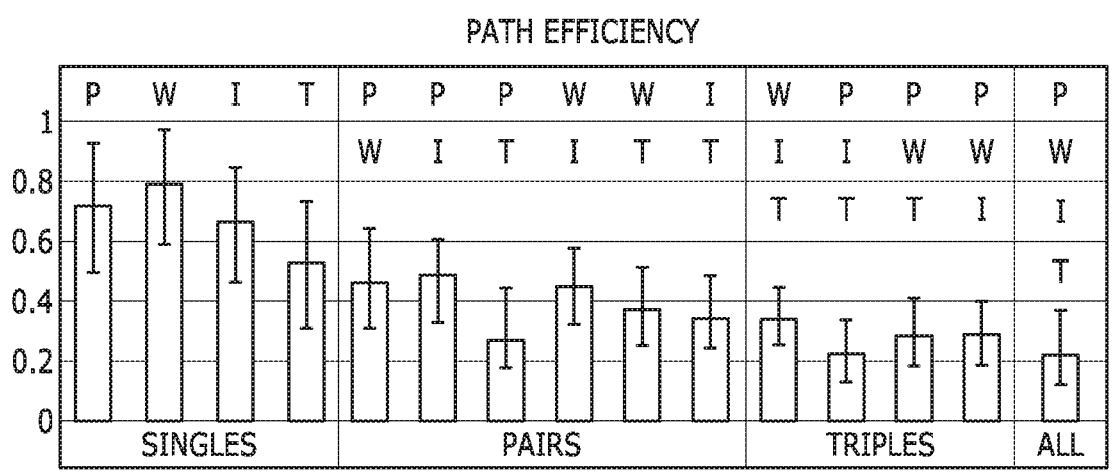

The prosthetic hand controller was evaluated in 3 degrees of freedom (DOF) 1- and 9-months post-training in both subjects. Targets covered all gross combinations of movements in 3D space in random proportions, emphasizing the controller's ability to match a variety of targets. All metrics are presented as compared to the subjects' intact hands (zero line), for which average performance values are listed in the legend of the top set of graphs as shown in FIG. 14. As shown in the top set of graphs in FIG. 14 the subjects were asked to match targets in 3 DOF using an R3 Delaunay controller. All targets were matched within 30 seconds, indicating reasonable control over the 3D space.

The prosthetic hand controller was also evaluated in 4 degrees of freedom over the course of roughly 12 months. All metrics are presented as compared to the subjects' intact hands (zero line), for which average performance values are listed in the legend of the middle and lower sets of graphs in FIG. 14. The middle set of graphs in FIG. 14 display a subject's ability to match targets in 4 DOF without retraining. Both controllers with 8 iEMG channels showed stable performance over 7+ months and a controller with 6 iEMG channels showed degradation over time. An additional Subject 2 (s2) Th set is present in the three months period with set two. The lower set of graphs in FIG. 14 show the performance of the S2 controller in a more robust target set. S2 was asked to match 40 targets involving between 1 and 4 combined movements. The time taken to complete the movements and the path efficiencies to match the movements were measured for each of the 40 targets. This shows that performance markedly decreases as task difficulty increases. No kinematic comparison was made so no comparison with other controllers is available.

Figure 15:
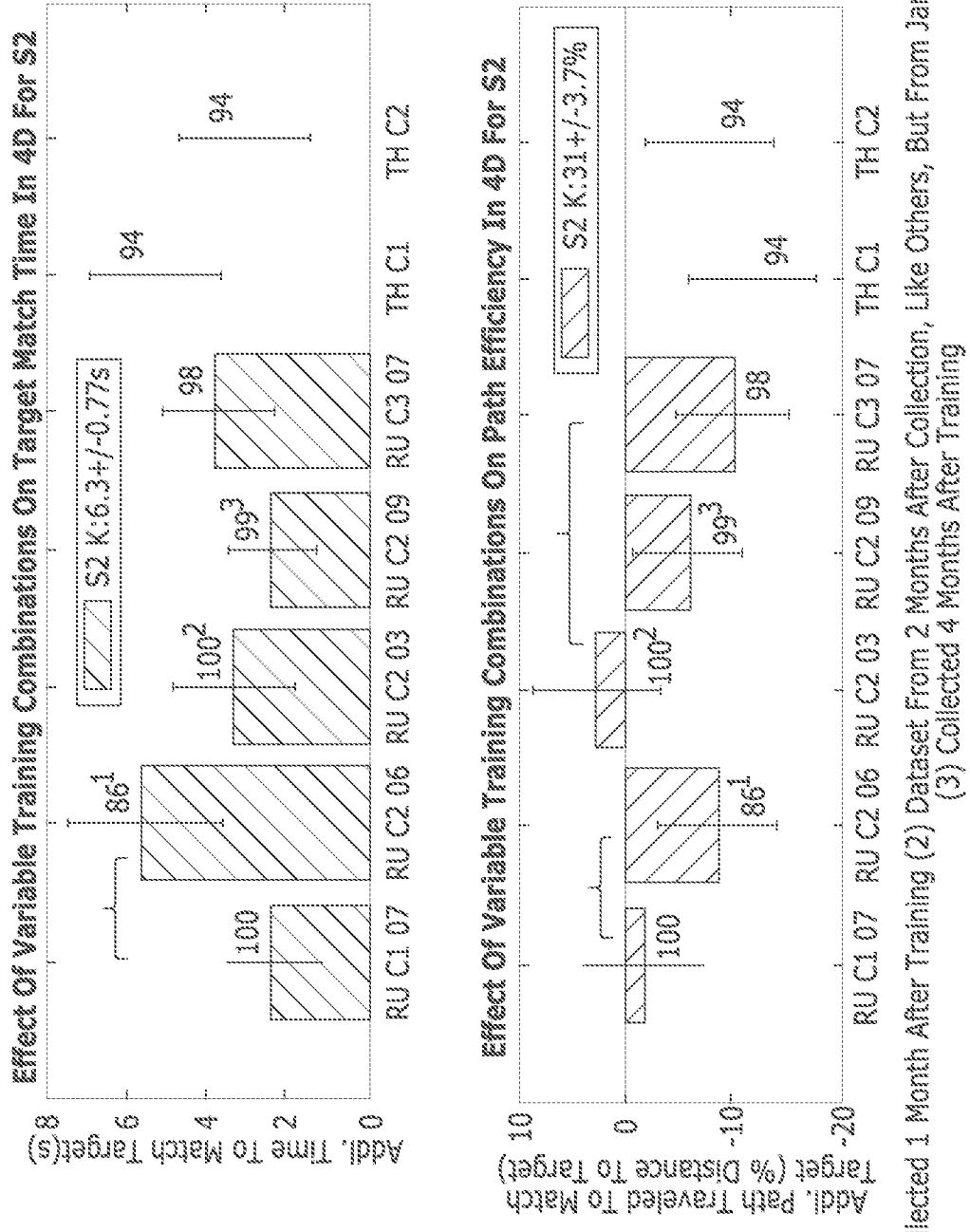
FIG. 15 is a graphical representation showing experimental results showing the effect of variable training combinations on target match time and path efficiency.

Several variations on the controller were evaluated in this study. The 'base' case combined 3 of 5 movement repetitions to find the EMG pattern for each movement—with the two outliers sequentially removed based off their distance from the mean pattern. One reduced data case—reduced repetitions—only kept the median of these three. After retraining to include more combinations of movements roughly 4 months after beginning the study, additional cases involving only 1 or combinations of all 3 movements were considered separately. As shown in FIGS. 15, C1, C2, and C3 indicate the number of movements combined in each training set. C1, for instance, includes only single movements in each of the 4 degrees of freedom. C2, the default, indicates that both single and paired movements were made available to the controller. Subject 2 (S2) was asked to match targets with the controller being provided an expanded/reduced number of movement classes for training. For scheduling reasons, this was done two months after training, while comparative datasets were collected one and four months after training, which indicates improvement in controllability. For further comparison, the performance of a prior dataset at a two-month period is also provided in FIG. 15. The high match rate indicates that the controller, trained on a reduced number of movement combinations, still provides reasonable control in 4D.

Figure 16:
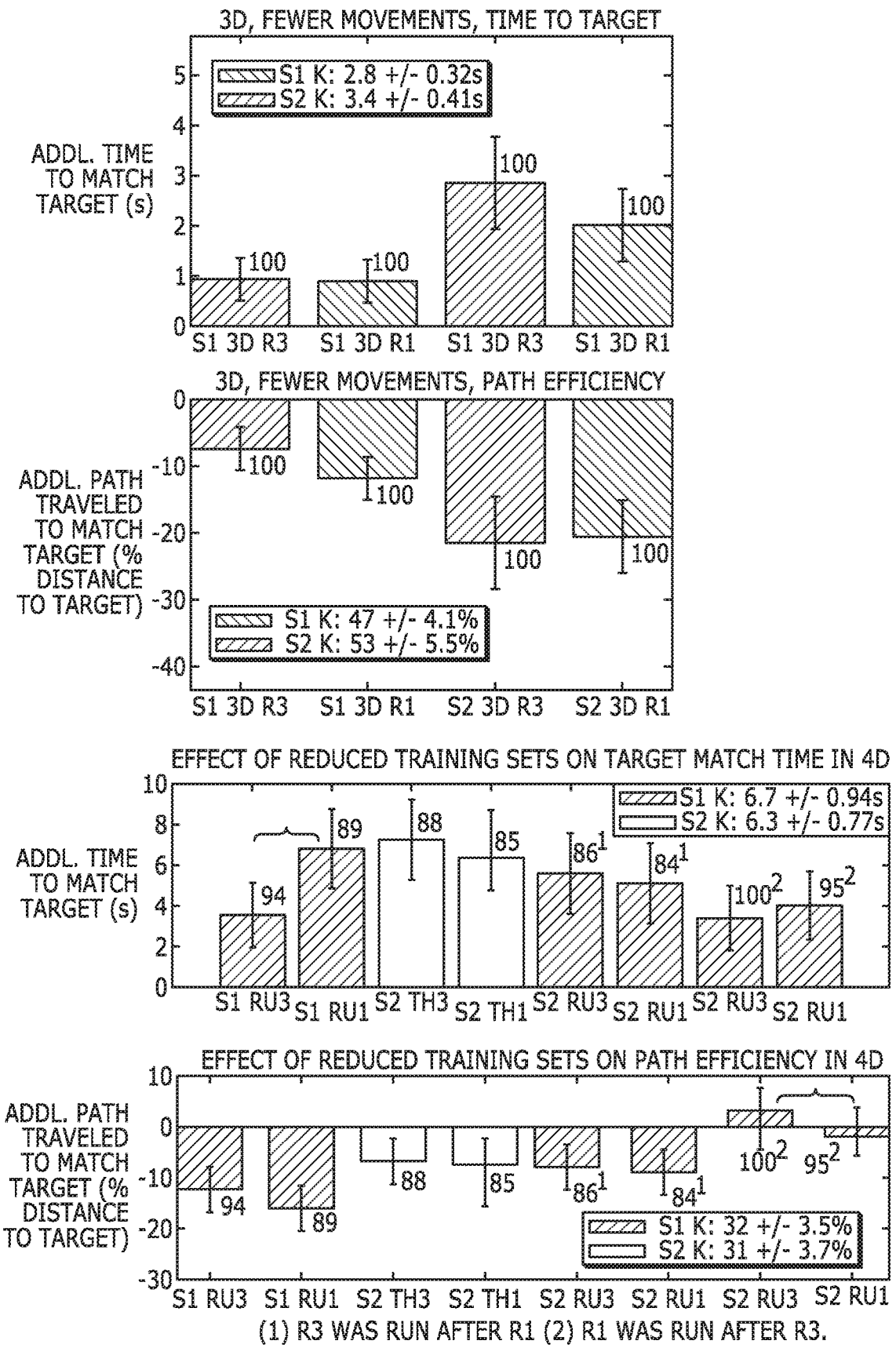
FIG. 16 is a graphical representation showing experimental results showing the effect of repetitions of each movement on time to target and path efficiency and the effect of reduced training sets on target match time and path efficiency.

The controller was also evaluated in a case where one repetition of each movement was kept, rather than using the average of 3 of 5 movements as represented in the results displayed in FIG. 16. As shown in FIG. 16, the controller was evaluated with a reduced number of training repetitions to demonstrate robustness to small training sets as well as hypothetical performance given a training set from a skilled user. Of the five movement repetitions collected, two outliers were first removed, then the remaining three were either averaged (R3) or the median (R1) was kept to build the Delaunay triangulation. The comparable match rates and metrics indicate robustness in the small training sets.

From the above description, those skilled in the art will perceive improvements, changes and modifications. Such improvements, changes and modifications are within the skill of one in the art and are intended to be covered by the appended claims.

The following is claimed:

1. A method, comprising:
    receiving, by a system comprising a processor, user-specific EMG signals recorded by electrodes located on a limb of a user, wherein the user-specific EMG signals comprise one or more EMG patterns that indicate a single movement;
    decomposing, by the system, the user-specific EMG signals into the one or more EMG patterns in EMG feature space that indicate the single movement;
    updating, by the system, a user-specific model of muscular activity to include the single movement and corresponding one or more primary muscle patterns based on the one or more EMG patterns in EMG feature space; and
    controlling, by the system, the external device based on a predicted intent of the user to move the external device using the user-specific model of muscular activity by:
        receiving an unknown EMG signal from the user,
        identifying a partition of the EMG feature space where the unknown EMG signal is located,
        bounding the partition of the EMG feature space where the unknown EMG signal is located by known single movements with a corresponding one or more primary muscle patterns, and
        determining a ratio of movement vectors that should be combined to determine the direction and the magnitude of the intent of the user to move the external device, wherein the ratio of movement vectors corresponds to the unknown EMG signal.

2. The method of claim 1, wherein the receiving the user-generated EMG signals further comprises:
    displaying a visualization of a number of combinations of movements; and
    prompting the user to move the limb of the user to match the visualization.

3. The method of claim 2, wherein the movements comprise wrist flexion/extension, wrist pronation/supination, D2 flexion/extension, thumb palmer movement, thumb lateral movement, wrist radial/ulnar deviation, and D3-D5 flexion/extension.

4. The method of claim 1, wherein the updating the user-specific model further comprises:
    extracting a feature from each the one or more EMG patterns in EMG feature space that indicate the single movement, wherein each of the user specific EMG signals is recorded by a different electrode;
    determining, by a fitting method, the one or more primary muscle patterns for the feature;
    generating the EMG feature space based on the feature extracted for the single movement;
    partitioning the EMG feature space into a tetrahedra of N+1 vertices; and
    generating a Triangulated Irregular Network based on the tetrahedra of N+1 vertices, wherein the Triangulated Irregular Network corresponds to the user-specific model of muscular activity.

5. The method of claim 4, wherein the EMG feature space is partitioned with Delaunay Triangulation, wherein the EMG feature space is divided into the tetrahedra with a maximized minimum internal angle.

6. The method of claim 4, wherein the feature is a mean absolute value.

7. The method of claim 4, wherein the primary muscle patterns for the feature are determined by Principal Component Analysis.

8. The method of claim 4, wherein the one or more primary muscle patterns are fixed ratios of muscle synergies.

9. The method of claim 1, wherein the electrodes are implanted in at least two muscles of the limb of the user.

10. The method of claim 9, wherein the at least two muscles comprise at least two of a Pronator, a Flexor Carpi Radialis (FCR), a Flexor Digitorum Superficialis (FDS), a Flexor Carpi Ulnaris (FCU), a Supinator, an Extensor Carpi Radialis Longus (ECRL), an Extensor Digitorum (ED), or an Extensor Carpi Ulnaris (ECU).

11. The method of claim 1, wherein the external device is one of a prosthetic limb, a robotic system, or a virtual system.

12. A system, comprising:
    at least one electrode configured to be located on a limb of a user; and
    a controller, coupled to the at least one electrode, comprising:
        a non-transitory memory storing instructions; and
        a processor to execute the instruction stored in the memory to at least:
            receive user-specific EMG signals recorded by electrodes located on a limb of a user, wherein the user-specific EMG signals comprise one or more EMG patterns that indicate a single movement;
            decompose the user-specific EMG signals into the one or more EMG patterns in EMG feature space that indicate the single movement;
            update a user-specific model of muscular activity to include the single movement and corresponding one or more primary muscle patterns based on the one or more EMG patterns in EMG feature space; and
            predict an intent of the user to move the external device based on the user-specific model of muscular activity by:

identifying a partition of the EMG feature space where the unknown EMG signal is located;

bounding the partition of the EMG feature space where the unknown EMG signal is located by known single movements with a corresponding one or more primary muscle patterns; and determining a ratio of movement vectors that should be combined to determine the direction and the magnitude of the intent of the user to move the external device, wherein the ratio of movement vectors corresponds to the unknown EMG signal, wherein the user-specific model of muscular activity is used to control an external device based on muscular activity in the limb of the user.

13. The system of claim 12, wherein the system further comprises:

a display device coupled to the controller and configured to:

display a visualization of a number of combinations of movements; and prompt the user to move the limb of the user to match the visualization.

14. The system of claim 12, wherein the user-specific model is updated by:

extracting a feature from each the one or more EMG patterns in EMG feature space that indicate the single movement, wherein each of the user specific EMG signals is recorded by a different electrode;

determining, by a fitting method, the one or more primary muscle patterns for the feature;

generating the EMG feature space based on the feature extracted for the single movement;

partitioning the EMG feature space into a tetrahedra of N+1 vertices; and generating a Triangulated Irregular Network based on the tetrahedra of N+1 vertices, wherein the Triangulated Irregular Network corresponds to the user-specific model of muscular activity.

15. The system of claim 14, wherein the EMG feature space is partitioned with Delaunay Triangulation, wherein the EMG feature space is divided into the tetrahedra with a maximized minimum internal angle.

16. The system of claim 14, wherein the feature is a mean absolute value.

17. The system of claim 14, wherein the primary muscle patterns for the feature are determined by Principal Component Analysis.

18. The system of claim 12, wherein the electrodes are implanted in at least two muscles of the limb of the user.

19. The system of claim 18, wherein the at least two muscles comprise at least two of a Pronator, a Flexor Carpi Radialis (FCR), a Flexor Digitorum Superficialis (FDS), a Flexor Carpi Ulnaris (FCU), a Supinator, an Extensor Carpi Radialis Longus (ECRL), an Extensor Digitorum (ED) or an Extensor Carpi Ulnaris (ECU).

20. The system of claim 12, wherein the external device is one of a prosthetic limb, a robotic system, or a virtual system.

21. A method, comprising:

receiving, by a system comprising a processor, user-specific EMG signals recorded by electrodes located on a limb of a user, wherein the user-specific EMG signals comprise one or more EMG patterns that indicate a single movement;

decomposing, by the system, the user-specific EMG signals into the one or more EMG patterns in EMG feature space that indicate the single movement; and updating, by the system, a user-specific model of muscular activity to include the single movement and corresponding one or more primary muscle patterns by:

extracting a feature from each the one or more EMG patterns in EMG feature space that indicate the single movement, wherein each of the user specific EMG signals is recorded by a different electrode;

determining, by a fitting method, the one or more primary muscle patterns for the feature;

generating the EMG feature space based on the feature extracted for the single movement;

partitioning the EMG feature space into a tetrahedra of N+1 vertices; and generating a Triangulated Irregular Network based on the tetrahedra of N+1 vertices, wherein the Triangulated Irregular Network corresponds to the user-specific model of muscular activity, wherein the user-specific model of muscular activity is used to control an external device based on muscular activity in the limb of the user.

* * * * *